US012698776B2

(12) United States Patent
Yanai et al.

(10) Patent No.: US 12,698,776 B2
(45) Date of Patent: Aug. 4, 2026

(54) ALTERNATING PUMP GAPS

(71) Applicant: TC1 LLC, St. Paul, MN (US)

(72) Inventors: Masamichi Yanai, Ann Arbor, MI (US); Shunzhou Yu, Ann Arbor, MI (US); Tao Zhang, Ann Arbor, MI (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 19/181,780

(22) Filed: Apr. 17, 2025

(65) Prior Publication Data

US 2025/0361867 A1 Nov. 27, 2025

Related U.S. Application Data

(63) Continuation of application No. 18/241,433, filed on Sep. 1, 2023, now Pat. No. 12,297,836, which is a
(Continued)

(51) Int. Cl.
*F04D 13/06* (2006.01)
*A61M 60/232* (2021.01)
(Continued)

(52) U.S. Cl.
CPC ......... *F04D 13/064* (2013.01); *A61M 60/232* (2021.01); *A61M 60/237* (2021.01);
(Continued)

(58) Field of Classification Search
CPC . A61M 1/1031; A61M 1/122; F04D 13/0666; F04D 13/024; F04D 13/027;
(Continued)

(56) References Cited

U.S. PATENT DOCUMENTS

| | | | |
|---|---|---|---|
| 1,093,868 A | 4/1914 | Leighty | |
| 2,684,035 A | 7/1954 | Kemp | |

(Continued)

FOREIGN PATENT DOCUMENTS

| | | | |
|---|---|---|---|
| CN | 1347585 A | 5/2002 | |
| CN | 1 462344 A | 12/2003 | |

(Continued)

OTHER PUBLICATIONS

Asama et al., "A Compact Highly Efficient and Low Hemolytic Centrifugal Blood Pump with a Magnetically Levitated Impeller", Artificial Organs, vol. 30, No. 3, Mar. 1, 2006, pp. 160-167.
(Continued)

*Primary Examiner* — Kenneth J Hansen
(74) *Attorney, Agent, or Firm* — Kilpatrick Townsend & Stockton LLP

(57) ABSTRACT

A mechanical circulatory support system includes a ventricular assist device, a percutaneous cable, an external control unit, and an external power source. The ventricular assist device includes a housing, an impeller, levitation magnets, a stator assembly, and control electronics. The impeller includes a first annular disk, a second annular disk, centrifugal impeller blades, first magnet segments, and second magnet segments. The stator assembly includes stator coils operable to rotate the impeller and apply a first positioning force to the impeller. The levitation magnets apply a second positioning force to the impeller. The control electronics are configured to control currents supplied to the stator coils to control rotation of the impeller and to control the first positioning force applied to the impeller to control an axial position of the impeller within the housing.

20 Claims, 16 Drawing Sheets

Related U.S. Application Data continuation of application No. 17/240,204, filed on Apr. 26, 2021, now Pat. No. 11,781,551, which is a continuation of application No. 16/443,471, filed on Jun. 17, 2019, now Pat. No. 11,015,605, which is a continuation of application No. 15/041,987, filed on Feb. 11, 2016, now Pat. No. 10,371,152.

(60) Provisional application No. 62/115,318, filed on Feb. 12, 2015.

(51) Int. Cl.

| | |
|---|---|
| *A61M 60/237* | (2021.01) |
| *A61M 60/422* | (2021.01) |
| *A61M 60/538* | (2021.01) |
| *A61M 60/82* | (2021.01) |
| *A61M 60/824* | (2021.01) |
| *F04D 29/047* | (2006.01) |
| *F04D 29/048* | (2006.01) |

(52) U.S. Cl.
CPC ........ *A61M 60/422* (2021.01); *A61M 60/538* (2021.01); *A61M 60/82* (2021.01); *A61M 60/824* (2021.01); *F04D 13/0646* (2013.01); *F04D 13/0666* (2013.01); *F04D 29/047* (2013.01); *F04D 29/048* (2013.01); *A61M 2205/3334* (2013.01)

(58) Field of Classification Search
CPC .. F04D 13/0646; F04D 29/048; F04D 29/026; F04D 29/041
See application file for complete search history.

(56) References Cited

U.S. PATENT DOCUMENTS

| 3,023,334 A | 2/1962 | Burr et al. |
|---|---|---|
| 3,510,229 A | 5/1970 | Smith |
| 3,620,638 A | 11/1971 | Kaye et al. |
| 3,870,382 A | 3/1975 | Reinhoudt |
| 3,932,069 A | 1/1976 | Giardini et al. |
| 3,960,468 A | 6/1976 | Boorse et al. |
| 4,149,535 A | 4/1979 | Volder |
| 4,382,199 A | 5/1983 | Isaacson |
| 4,392,836 A | 7/1983 | Sugawara |
| 4,434,389 A | 2/1984 | Langley et al. |
| 4,507,048 A | 3/1985 | Belenger et al. |
| 4,528,485 A | 7/1985 | Boyd, Jr. |
| 4,540,402 A | 9/1985 | Aigner |
| 4,549,860 A | 10/1985 | Yakich |
| 4,645,961 A | 2/1987 | Malsky |
| 4,686,982 A | 8/1987 | Nash |
| 4,688,998 A | 8/1987 | Olsen et al. |
| 4,753,221 A | 6/1988 | Kensey et al. |
| 4,763,032 A | 8/1988 | Bramm et al. |
| 4,769,006 A | 9/1988 | Papantonakos |
| 4,779,614 A | 10/1988 | Moise |
| 4,790,843 A | 12/1988 | Carpentier et al. |
| 4,806,080 A | 2/1989 | Mizobuchi et al. |
| 4,814,677 A | 3/1989 | Plunkett |
| 4,817,586 A | 4/1989 | Wampler |
| 4,846,152 A | 7/1989 | Wampler et al. |
| 4,857,781 A | 8/1989 | Shih |
| 4,888,011 A | 12/1989 | Kung et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,930,997 A | 6/1990 | Bennett |
| 4,944,722 A | 7/1990 | Carriker et al. |
| 4,957,504 A | 9/1990 | Chardack |
| 4,964,864 A | 10/1990 | Summers et al. |
| 4,969,865 A | 11/1990 | Hwang et al. |
| 4,985,014 A | 1/1991 | Orejola |
| 4,995,857 A | 2/1991 | Arnold |
| 5,021,048 A | 6/1991 | Buckholtz |
| 5,078,741 A | 1/1992 | Bramm et al. |
| 5,092,844 A | 3/1992 | Schwartz et al. |
| 5,092,879 A | 3/1992 | Jarvik |
| 5,100,374 A | 3/1992 | Kageyama |
| 5,106,263 A | 4/1992 | Irie |
| 5,106,273 A | 4/1992 | Lemarquand et al. |
| 5,106,372 A | 4/1992 | Ranford |
| 5,112,202 A | 5/1992 | Oshima et al. |
| 5,112,349 A | 5/1992 | Summers et al. |
| 5,129,883 A | 7/1992 | Black |
| 5,145,333 A | 9/1992 | Smith |
| 5,147,186 A | 9/1992 | Buckholtz |
| 5,190,528 A | 3/1993 | Fonger et al. |
| 5,201,679 A | 4/1993 | Velte, Jr. et al. |
| 5,211,546 A | 5/1993 | Isaacson et al. |
| 5,229,693 A | 7/1993 | Futami et al. |
| 5,275,580 A | 1/1994 | Yamazaki |
| 5,290,227 A | 3/1994 | Pasque |
| 5,290,236 A | 3/1994 | Mathewson |
| 5,300,112 A | 4/1994 | Barr |
| 5,306,295 A | 4/1994 | Kolff et al. |
| 5,312,341 A | 5/1994 | Turi |
| 5,313,128 A | 5/1994 | Robinson et al. |
| 5,332,374 A | 7/1994 | Kricker et al. |
| 5,346,458 A | 9/1994 | Affeld |
| 5,350,283 A | 9/1994 | Nakazeki et al. |
| 5,354,331 A | 10/1994 | Schachar |
| 5,360,445 A | 11/1994 | Goldowsky |
| 5,370,509 A | 12/1994 | Golding et al. |
| 5,376,114 A | 12/1994 | Jarvik |
| 5,385,581 A | 1/1995 | Bramm et al. |
| 5,405,383 A | 4/1995 | Barr |
| 5,449,342 A | 9/1995 | Hirose et al. |
| 5,478,222 A | 12/1995 | Heidelberg et al. |
| 5,504,978 A | 4/1996 | Meyer, III |
| 5,507,629 A | 4/1996 | Jarvik |
| 5,519,270 A | 5/1996 | Yamada et al. |
| 5,533,957 A | 7/1996 | Aldea |
| 5,569,111 A | 10/1996 | Cho et al. |
| 5,575,630 A | 11/1996 | Nakazawa et al. |
| 5,588,812 A | 12/1996 | Taylor et al. |
| 5,595,762 A | 1/1997 | Derrieu et al. |
| 5,611,679 A | 3/1997 | Ghosh et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman, Jr. et al. |
| 5,695,471 A | 12/1997 | Wampler |
| 5,708,346 A | 1/1998 | Schob |
| 5,725,357 A | 3/1998 | Nakazeki et al. |
| 5,738,649 A | 4/1998 | Macoviak |
| 5,746,575 A | 5/1998 | Westphal et al. |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,795,074 A | 8/1998 | Rahman et al. |
| 5,800,559 A | 9/1998 | Higham et al. |
| 5,807,311 A | 9/1998 | Palestrant |
| 5,814,011 A | 9/1998 | Corace |
| 5,824,069 A | 10/1998 | Lemole |
| 5,843,129 A | 12/1998 | Larson, Jr. et al. |
| 5,851,174 A | 12/1998 | Jarvik et al. |
| 5,853,394 A | 12/1998 | Tolkoff et al. |
| 5,868,702 A | 2/1999 | Stevens et al. |
| 5,868,703 A | 2/1999 | Bertolero et al. |
| 5,890,883 A | 4/1999 | Golding et al. |
| 5,911,685 A | 6/1999 | Siess et al. |
| 5,917,295 A | 6/1999 | Mongeau |
| 5,917,297 A | 6/1999 | Gerster et al. |
| 5,921,913 A | 7/1999 | Siess |
| 5,924,848 A | 7/1999 | Izraelev |
| 5,924,975 A | 7/1999 | Goldowsky |
| 5,928,131 A | 7/1999 | Prem |

(56)                References Cited

U.S. PATENT DOCUMENTS

| | | | |
|---|---|---|---|
| 5,938,412 | A | 8/1999 | Izraelev |
| 5,941,813 | A | 8/1999 | Sievers et al. |
| 5,945,753 | A | 8/1999 | Maegawa et al. |
| 5,947,703 | A | 9/1999 | Nojiri et al. |
| 5,951,263 | A | 9/1999 | Taylor et al. |
| 5,964,694 | A | 10/1999 | Siess et al. |
| 5,984,892 | A | 11/1999 | Bedingham |
| 6,004,269 | A | 12/1999 | Crowley et al. |
| 6,007,479 | A | 12/1999 | Rottenberg et al. |
| 6,030,188 | A | 2/2000 | Nojiri et al. |
| 6,042,347 | A | 3/2000 | Scholl et al. |
| 6,053,705 | A | 4/2000 | Schob et al. |
| 6,058,593 | A | 5/2000 | Siess |
| 6,066,086 | A | 5/2000 | Antaki et al. |
| 6,071,093 | A | 6/2000 | Hart |
| 6,074,180 | A | 6/2000 | Khanwilkar et al. |
| 6,080,133 | A | 6/2000 | Wampler |
| 6,082,900 | A | 7/2000 | Takeuchi et al. |
| 6,083,260 | A | 7/2000 | Aboul-Hosn |
| 6,086,527 | A | 7/2000 | Talpade |
| 6,100,618 | A | 8/2000 | Schoeb et al. |
| 6,123,659 | A | 9/2000 | le Blanc et al. |
| 6,123,726 | A | 9/2000 | Mori et al. |
| 6,139,487 | A | 10/2000 | Siess |
| 6,142,752 | A | 11/2000 | Akamatsu et al. |
| 6,143,025 | A | 11/2000 | Stobie et al. |
| 6,146,325 | A | 11/2000 | Lewis et al. |
| 6,149,683 | A | 11/2000 | Lancisi et al. |
| 6,158,984 | A | 12/2000 | Cao et al. |
| 6,171,078 | B1 | 1/2001 | Schob |
| 6,176,822 | B1 | 1/2001 | Nix et al. |
| 6,176,848 | B1 | 1/2001 | Rau et al. |
| 6,179,773 | B1 | 1/2001 | Prem et al. |
| 6,190,304 | B1 | 2/2001 | Downey et al. |
| 6,200,260 | B1 | 3/2001 | Bolling |
| 6,206,659 | B1 | 3/2001 | Izraelev |
| 6,222,290 | B1 | 4/2001 | Schob et al. |
| 6,227,797 | B1 | 5/2001 | Watterson et al. |
| 6,227,820 | B1 | 5/2001 | Jarvik |
| 6,234,772 | B1 | 5/2001 | Wampler et al. |
| 6,234,998 | B1 | 5/2001 | Wampler |
| 6,245,007 | B1 | 6/2001 | Bedingham et al. |
| 6,247,892 | B1 | 6/2001 | Kazatchkov et al. |
| 6,249,067 | B1 | 6/2001 | Schob et al. |
| 6,254,359 | B1 | 7/2001 | Aber |
| 6,264,635 | B1 | 7/2001 | Wampler et al. |
| 6,268,675 | B1 | 7/2001 | Amrhein |
| 6,276,831 | B1 | 8/2001 | Takahashi et al. |
| 6,293,901 | B1 | 9/2001 | Prem |
| 6,295,877 | B1 | 10/2001 | Aboul-Hosn et al. |
| 6,319,231 | B1 | 11/2001 | Andrulitis |
| 6,320,731 | B1 | 11/2001 | Eaves et al. |
| 6,351,048 | B1 | 2/2002 | Schob et al. |
| 6,355,998 | B1 | 3/2002 | Schob et al. |
| 6,365,996 | B2 | 4/2002 | Schob |
| 6,375,607 | B1 | 4/2002 | Prem |
| 6,387,037 | B1 | 5/2002 | Bolling et al. |
| 6,394,769 | B1 | 5/2002 | Bearnson et al. |
| 6,422,990 | B1 | 7/2002 | Prem |
| 6,425,007 | B1 | 7/2002 | Messinger |
| 6,428,464 | B1 | 8/2002 | Bolling |
| 6,439,845 | B1 | 8/2002 | Veres |
| 6,447,266 | B2 | 9/2002 | Antaki et al. |
| 6,447,441 | B1 | 9/2002 | Yu et al. |
| 6,458,163 | B1 | 10/2002 | Slemker et al. |
| 6,508,777 | B1 | 1/2003 | Macoviak et al. |
| 6,508,787 | B2 | 1/2003 | Erbel et al. |
| 6,517,315 | B2 | 2/2003 | Belady |
| 6,522,093 | B1 | 2/2003 | Hsu et al. |
| 6,532,964 | B2 | 3/2003 | Aboul-Hosn et al. |
| 6,533,716 | B1 | 3/2003 | Schmitz-Rode et al. |
| 6,544,216 | B1 | 4/2003 | Sammler et al. |
| 6,547,519 | B2 | 4/2003 | deBlanc et al. |
| 6,547,530 | B2 | 4/2003 | Ozaki et al. |
| 6,575,717 | B2 | 6/2003 | Ozaki et al. |
| 6,589,030 | B2 | 7/2003 | Ozaki |
| 6,595,762 | B2 | 7/2003 | Khanwilkar et al. |
| 6,605,032 | B2 | 8/2003 | Benkowski et al. |
| 6,609,883 | B2 | 8/2003 | Woodard et al. |
| 6,610,004 | B2 | 8/2003 | Viole et al. |
| 6,623,420 | B2 | 9/2003 | Reich et al. |
| 6,641,378 | B2 | 11/2003 | Davis et al. |
| 6,641,558 | B1 | 11/2003 | Aboul-Hosn et al. |
| 6,688,861 | B2 | 2/2004 | Wampler |
| 6,692,318 | B2 | 2/2004 | McBride |
| 6,698,097 | B1 | 3/2004 | Miura et al. |
| 6,709,418 | B1 | 3/2004 | Aboul-Hosn et al. |
| 6,716,157 | B2 | 4/2004 | Goldowsky |
| 6,716,189 | B1 | 4/2004 | Jarvik et al. |
| 6,732,501 | B2 | 5/2004 | Yu et al. |
| 6,749,598 | B1 | 6/2004 | Keren et al. |
| 6,776,578 | B2 | 8/2004 | Belady |
| 6,790,171 | B1 | 9/2004 | Grundeman et al. |
| 6,794,789 | B2 | 9/2004 | Siess et al. |
| 6,808,371 | B2 | 10/2004 | Niwatsukino et al. |
| 6,817,836 | B2 | 11/2004 | Nose et al. |
| 6,846,168 | B2 | 1/2005 | Davis et al. |
| 6,860,713 | B2 | 3/2005 | Hoover |
| 6,884,210 | B2 | 4/2005 | Nose et al. |
| 6,926,662 | B1 | 8/2005 | Aboul-Hosn et al. |
| 6,935,344 | B1 | 8/2005 | Aboul-Hosn et al. |
| 6,942,672 | B2 | 9/2005 | Heilman et al. |
| 6,949,066 | B2 | 9/2005 | Bearnson et al. |
| 6,966,748 | B2 | 11/2005 | Woodard et al. |
| 6,974,436 | B1 | 12/2005 | Aboul-Hosn et al. |
| 6,991,595 | B2 | 1/2006 | Burke et al. |
| 7,010,954 | B2 | 3/2006 | Siess et al. |
| 7,011,620 | B1 | 3/2006 | Siess |
| 7,022,100 | B1 | 4/2006 | Aboul-Hosn et al. |
| 7,027,875 | B2 | 4/2006 | Siess et al. |
| 7,048,681 | B2 | 5/2006 | Tsubouchi et al. |
| 7,089,059 | B1 | 8/2006 | Pless |
| 7,090,401 | B2 | 8/2006 | Rahman et al. |
| 7,112,903 | B1 | 9/2006 | Schob |
| 7,122,019 | B1 | 10/2006 | Kesten et al. |
| 7,128,538 | B2 | 10/2006 | Tsubouchi et al. |
| 7,156,802 | B2 | 1/2007 | Woodard et al. |
| 7,160,243 | B2 | 1/2007 | Medvedev |
| 7,172,551 | B2 | 2/2007 | Leasure |
| 7,175,588 | B2 | 2/2007 | Morello |
| 7,202,582 | B2 | 4/2007 | Eckert et al. |
| 7,241,257 | B1 | 7/2007 | Ainsworth et al. |
| 7,284,956 | B2 | 10/2007 | Nose et al. |
| 7,329,236 | B2 | 2/2008 | Kesten et al. |
| 7,331,921 | B2 | 2/2008 | Viole et al. |
| 7,335,192 | B2 | 2/2008 | Keren et al. |
| 7,393,181 | B2 | 7/2008 | McBride et al. |
| 7,431,688 | B2 | 10/2008 | Wampler et al. |
| 7,462,019 | B1 | 12/2008 | Allarie et al. |
| 7,467,930 | B2 | 12/2008 | Ozaki et al. |
| 7,470,246 | B2 | 12/2008 | Mori et al. |
| 7,476,077 | B2 | 1/2009 | Woodard et al. |
| 7,491,163 | B2 | 2/2009 | Viole et al. |
| 7,575,423 | B2 | 8/2009 | Wampler |
| 7,645,225 | B2 | 1/2010 | Medvedev et al. |
| 7,660,635 | B1 | 2/2010 | Verness et al. |
| 7,699,586 | B2 | 4/2010 | LaRose et al. |
| 7,731,675 | B2 | 6/2010 | Aboul-Hosn et al. |
| 7,748,964 | B2 | 7/2010 | Yaegashi et al. |
| 7,802,966 | B2 | 9/2010 | Wampler et al. |
| 7,841,976 | B2 | 11/2010 | McBride et al. |
| 7,862,501 | B2 | 1/2011 | Woodard |
| 7,888,242 | B2 | 2/2011 | Tanaka et al. |
| 7,934,909 | B2 | 5/2011 | Nuesser et al. |
| 7,972,122 | B2 | 7/2011 | LaRose et al. |
| 7,976,271 | B2 | 7/2011 | LaRose et al. |
| 7,997,854 | B2 | 8/2011 | LaRose et al. |
| 8,007,254 | B2 | 8/2011 | LaRose et al. |
| 8,096,935 | B2 | 1/2012 | Sutton et al. |
| 8,123,669 | B2 | 2/2012 | Siess et al. |
| 8,152,493 | B2 | 4/2012 | LaRose et al. |
| 8,177,703 | B2 | 5/2012 | Smith et al. |
| 8,226,373 | B2 | 7/2012 | Yaegashi |
| 8,282,359 | B2 | 10/2012 | Ayre et al. |

(56)     References Cited

U.S. PATENT DOCUMENTS

| | | | |
|---|---|---|---|
| 8,283,829 | B2 | 10/2012 | Yamamoto et al. |
| 8,366,381 | B2 | 2/2013 | Woodard et al. |
| 8,403,823 | B2 | 3/2013 | Yu et al. |
| 8,512,012 | B2 | 8/2013 | Akdis et al. |
| 8,535,211 | B2 | 9/2013 | Campbell et al. |
| 8,585,290 | B2 | 11/2013 | Bauer |
| 8,652,024 | B1 | 2/2014 | Yanai et al. |
| 8,686,674 | B2 | 4/2014 | Bi et al. |
| 8,770,945 | B2 | 7/2014 | Ozaki et al. |
| 8,821,365 | B2 | 9/2014 | Ozaki et al. |
| 8,827,661 | B2 | 9/2014 | Mori |
| 8,864,644 | B2 | 10/2014 | Yomtov |
| 8,870,552 | B2 | 10/2014 | Ayre et al. |
| 8,968,174 | B2 | 3/2015 | Yanai et al. |
| 9,039,595 | B2 | 5/2015 | Ayre et al. |
| 9,067,005 | B2 | 6/2015 | Ozaki et al. |
| 9,068,572 | B2 | 6/2015 | Ozaki et al. |
| 9,109,601 | B2 | 8/2015 | Mori |
| 9,132,215 | B2 | 9/2015 | Ozaki et al. |
| 9,133,854 | B2 | 9/2015 | Okawa et al. |
| 9,371,826 | B2 | 6/2016 | Yanai et al. |
| 9,381,285 | B2 | 7/2016 | Ozaki et al. |
| 9,382,908 | B2 | 7/2016 | Ozaki et al. |
| 9,410,549 | B2 | 8/2016 | Ozaki et al. |
| 9,556,873 | B2 | 1/2017 | Yanai et al. |
| 10,371,152 | B2 | 8/2019 | Yanai et al. |
| 2001/0039369 | A1 | 11/2001 | Terentiev |
| 2002/0051711 | A1 | 5/2002 | Ozaki |
| 2002/0058994 | A1 | 5/2002 | Hill et al. |
| 2002/0094281 | A1 | 7/2002 | Khanwilkar et al. |
| 2002/0095210 | A1 | 7/2002 | Finnegan et al. |
| 2003/0023302 | A1 | 1/2003 | Moe et al. |
| 2003/0045772 | A1 | 3/2003 | Reich et al. |
| 2003/0072656 | A1 | 4/2003 | Niwatsukino et al. |
| 2003/0144574 | A1 | 7/2003 | Heilman et al. |
| 2003/0163019 | A1 | 8/2003 | Goldowsky |
| 2003/0199727 | A1 | 10/2003 | Burke et al. |
| 2003/0236488 | A1 | 12/2003 | Novak |
| 2003/0236490 | A1 | 12/2003 | Novak |
| 2004/0007515 | A1 | 1/2004 | Geyer |
| 2004/0015232 | A1 | 1/2004 | Shu et al. |
| 2004/0024285 | A1 | 2/2004 | Muckter |
| 2004/0030381 | A1 | 2/2004 | Shu |
| 2004/0064012 | A1 | 4/2004 | Yanai |
| 2004/0143151 | A1 | 7/2004 | Mori et al. |
| 2004/0145337 | A1 | 7/2004 | Morishita |
| 2004/0152944 | A1 | 8/2004 | Medvedev et al. |
| 2004/0171905 | A1 | 9/2004 | Yu et al. |
| 2004/0210305 | A1 | 10/2004 | Shu et al. |
| 2004/0215050 | A1 | 10/2004 | Morello |
| 2004/0263341 | A1 | 12/2004 | Enzinna |
| 2005/0004418 | A1 | 1/2005 | Morello |
| 2005/0008496 | A1 | 1/2005 | Tsubouchi et al. |
| 2005/0025630 | A1 | 2/2005 | Ayre et al. |
| 2005/0043665 | A1 | 2/2005 | Vinci et al. |
| 2005/0073273 | A1 | 4/2005 | Maslov et al. |
| 2005/0089422 | A1 | 4/2005 | Ozaki et al. |
| 2005/0131271 | A1 | 6/2005 | Benkowski et al. |
| 2005/0141887 | A1 | 6/2005 | Lelkes |
| 2005/0194851 | A1 | 9/2005 | Eckert et al. |
| 2005/0261542 | A1 | 11/2005 | Riehl |
| 2005/0287022 | A1 | 12/2005 | Yaegashi et al. |
| 2006/0024182 | A1 | 2/2006 | Akdis et al. |
| 2006/0055274 | A1 | 3/2006 | Kim |
| 2006/0127227 | A1 | 6/2006 | Mehlhorn et al. |
| 2007/0073393 | A1 | 3/2007 | Kung et al. |
| 2007/0078293 | A1 | 4/2007 | Shambaugh, Jr. et al. |
| 2007/0095648 | A1 | 5/2007 | May et al. |
| 2007/0114961 | A1 | 5/2007 | Schwarzkopf |
| 2007/0134993 | A1 | 6/2007 | Tamez et al. |
| 2007/0189648 | A1 | 8/2007 | Kita et al. |
| 2007/0213690 | A1 | 9/2007 | Phillips et al. |
| 2007/0231135 | A1 | 10/2007 | Wampler et al. |
| 2007/0253842 | A1 | 11/2007 | Horvath et al. |
| 2007/0282298 | A1 | 12/2007 | Mason |
| 2007/0297923 | A1 | 12/2007 | Tada |
| 2008/0007196 | A1 | 1/2008 | Tan et al. |
| 2008/0021394 | A1 | 1/2008 | LaRose et al. |
| 2008/0030895 | A1 | 2/2008 | Obara et al. |
| 2008/0119777 | A1 | 5/2008 | Vinci et al. |
| 2008/0124231 | A1 | 5/2008 | Yaegashi |
| 2008/0183287 | A1 | 7/2008 | Ayre |
| 2008/0211439 | A1 | 9/2008 | Yokota et al. |
| 2008/0281146 | A1 | 11/2008 | Morello |
| 2009/0041595 | A1 | 2/2009 | Garzaniti et al. |
| 2009/0060743 | A1 | 3/2009 | McBride et al. |
| 2009/0074336 | A1 | 3/2009 | Engesser et al. |
| 2009/0099406 | A1 | 4/2009 | Salmonsen et al. |
| 2009/0171136 | A1 | 7/2009 | Shambaugh, Jr. |
| 2009/0257693 | A1 | 10/2009 | Aiello |
| 2009/0318834 | A1 | 12/2009 | Fujiwara et al. |
| 2010/0168534 | A1 | 7/2010 | Matsumoto et al. |
| 2010/0185280 | A1 | 7/2010 | Ayre et al. |
| 2010/0222634 | A1 | 9/2010 | Poirier |
| 2010/0234835 | A1 | 9/2010 | Horikawa et al. |
| 2010/0256440 | A1 | 10/2010 | Maher et al. |
| 2010/0262039 | A1 | 10/2010 | Fujiwara et al. |
| 2010/0266423 | A1 | 10/2010 | Gohean et al. |
| 2010/0305692 | A1 | 12/2010 | Thomas et al. |
| 2010/0324465 | A1 | 12/2010 | Vinci et al. |
| 2011/0015732 | A1 | 1/2011 | Kanebako |
| 2011/0112354 | A1 | 5/2011 | Nishimura et al. |
| 2011/0118766 | A1 | 5/2011 | Reichenbach et al. |
| 2011/0118829 | A1 | 5/2011 | Hoarau et al. |
| 2011/0118833 | A1 | 5/2011 | Reichenbach et al. |
| 2011/0129373 | A1 | 6/2011 | Mori |
| 2011/0160519 | A1 | 6/2011 | Arndt et al. |
| 2011/0218383 | A1 | 9/2011 | Broen et al. |
| 2011/0218384 | A1 | 9/2011 | Bachman et al. |
| 2011/0218385 | A1 | 9/2011 | Bolyard et al. |
| 2011/0237978 | A1 | 9/2011 | Fujiwara et al. |
| 2011/0243759 | A1* | 10/2011 | Ozaki ................. F04D 13/0666 |
| | | | 417/279 |
| 2011/0318203 | A1 | 12/2011 | Ozaki et al. |
| 2012/0003108 | A1 | 1/2012 | Ozaki et al. |
| 2012/0016178 | A1 | 1/2012 | Woodard et al. |
| 2012/0022645 | A1 | 1/2012 | Burke |
| 2012/0035411 | A1 | 2/2012 | LaRose et al. |
| 2012/0078030 | A1 | 3/2012 | Bourque |
| 2012/0078031 | A1 | 3/2012 | Burke et al. |
| 2012/0095280 | A1 | 4/2012 | Timms |
| 2012/0095281 | A1 | 4/2012 | Reichenbach et al. |
| 2012/0130152 | A1 | 5/2012 | Ozaki et al. |
| 2012/0226350 | A1 | 9/2012 | Rudser et al. |
| 2012/0243759 | A1 | 9/2012 | Fujisawa |
| 2012/0245681 | A1 | 9/2012 | Casas et al. |
| 2012/0253103 | A1 | 10/2012 | Robert |
| 2012/0308363 | A1 | 12/2012 | Ozaki et al. |
| 2013/0030240 | A1 | 1/2013 | Schima et al. |
| 2013/0121821 | A1 | 5/2013 | Ozaki et al. |
| 2013/0158521 | A1 | 6/2013 | Sobue |
| 2013/0170970 | A1 | 7/2013 | Ozaki et al. |
| 2013/0178694 | A1 | 7/2013 | Jeffery et al. |
| 2013/0225909 | A1 | 8/2013 | Dormanen et al. |
| 2013/0243623 | A1 | 9/2013 | Okawa et al. |
| 2013/0289334 | A1 | 10/2013 | Badstibner et al. |
| 2013/0331711 | A1 | 12/2013 | Mathur et al. |
| 2014/0030122 | A1 | 1/2014 | Ozaki et al. |
| 2014/0066690 | A1 | 3/2014 | Siebenhaar et al. |
| 2014/0066691 | A1 | 3/2014 | Siebenhaar |
| 2014/0100413 | A1 | 4/2014 | Casas et al. |
| 2014/0107399 | A1 | 4/2014 | Spence |
| 2014/0142367 | A1 | 5/2014 | Ayre et al. |
| 2014/0155682 | A1 | 6/2014 | Jeffery et al. |
| 2014/0200389 | A1 | 7/2014 | Yanai et al. |
| 2014/0205467 | A1 | 7/2014 | Yanai et al. |
| 2014/0241904 | A1 | 8/2014 | Yanai et al. |
| 2014/0275721 | A1 | 9/2014 | Yanai et al. |
| 2014/0275727 | A1 | 9/2014 | Bonde et al. |
| 2014/0296615 | A1 | 10/2014 | Franano |
| 2014/0309481 | A1 | 10/2014 | Medvedev et al. |
| 2014/0314597 | A1 | 10/2014 | Allaire et al. |
| 2014/0323796 | A1 | 10/2014 | Medvedev et al. |
| 2014/0343352 | A1 | 11/2014 | Arndt et al. |

(56) References Cited

U.S. PATENT DOCUMENTS

| | | |
|---|---|---|
| 2015/0017030 A1 | 1/2015 | Ozaki et al. |
| 2015/0023803 A1 | 1/2015 | Fritz et al. |
| 2015/0078936 A1 | 3/2015 | Mori |
| 2015/0306290 A1 | 10/2015 | Rosenberg et al. |
| 2015/0367048 A1 | 12/2015 | Brown et al. |
| 2015/0374892 A1 | 12/2015 | Yanai et al. |
| 2016/0058929 A1 | 3/2016 | Medvedev et al. |
| 2016/0058930 A1 | 3/2016 | Medvedev et al. |
| 2016/0228628 A1 | 8/2016 | Medvedev et al. |
| 2016/0235898 A1 | 8/2016 | Yanai et al. |
| 2016/0235899 A1 | 8/2016 | Yu et al. |
| 2016/0235900 A1 | 8/2016 | Yanai et al. |
| 2016/0281720 A1 | 9/2016 | Yanai et al. |
| 2016/0281728 A1 | 9/2016 | Ozaki et al. |

FOREIGN PATENT DOCUMENTS

| | | | |
|---|---|---|---|
| CN | 102239334 A | 11/2011 | |
| CN | 102341600 A | 2/2012 | |
| EP | 971212 A1 | 1/2000 | |
| EP | 1113117 A2 | 7/2001 | |
| EP | 1327455 A1 | 7/2003 | |
| EP | 1430919 A1 | 6/2004 | |
| EP | 1526286 A2 | 4/2005 | |
| EP | 1598087 A2 | 11/2005 | |
| EP | 1495773 A3 | 11/2006 | |
| EP | 2292282 A1 | 3/2011 | |
| EP | 2298375 A1 | 3/2011 | |
| EP | 2372160 A1 | 10/2011 | |
| EP | 2405140 A1 | 1/2012 | |
| EP | 2405141 A1 | 1/2012 | |
| EP | 2461465 A1 | 6/2012 | |
| EP | 2538086 A1 | 12/2012 | |
| EP | 2554191 A1 | 2/2013 | |
| EP | 2594799 A1 | 5/2013 | |
| EP | 2618001 A1 | 7/2013 | |
| EP | 2693609 A1 | 2/2014 | |
| EP | 2948202 A1 | 12/2015 | |
| EP | 2961987 A1 | 1/2016 | |
| EP | 3013385 A2 | 5/2016 | |
| EP | 3256186 A1 | 12/2017 | |
| EP | 2945662 B1 | 4/2018 | |
| JP | 589535 A | 1/1983 | |
| JP | 61293146 A | 12/1986 | |
| JP | 02007780 U | 1/1990 | |
| JP | 02033590 U | 3/1990 | |
| JP | 04091396 A | 3/1992 | |
| JP | 04148094 A | 5/1992 | |
| JP | 05021197 U | 3/1993 | |
| JP | 061 4538 U | 2/1994 | |
| JP | 06053790 U | 7/1994 | |
| JP | 06070476 U | 9/1994 | |
| JP | 06245455 A | 9/1994 | |
| JP | 07014220 U | 3/1995 | |
| JP | 07042869 U | 8/1995 | |
| JP | 07509156 A | 10/1995 | |
| JP | 09122228 A | 5/1997 | |
| JP | 10331841 A | 12/1998 | |
| JP | 11241695 A | 9/1999 | |
| JP | 11244377 A | 9/1999 | |
| JP | 2001309628 A | 11/2001 | |
| JP | 2002303288 A | 10/2002 | |
| JP | 2003501155 A | 1/2003 | |
| JP | 2003135592 A | 5/2003 | |
| JP | 2004166401 A | 6/2004 | |
| JP | 2004209240 A | 7/2004 | |
| JP | 2004332566 A | 11/2004 | |
| JP | 2004346925 A | 12/2004 | |
| JP | 2005094955 A | 4/2005 | |
| JP | 2005127222 A | 5/2005 | |
| JP | 2005245138 A | 9/2005 | |
| JP | 2005270345 A | 10/2005 | |
| JP | 2005270415 A | 10/2005 | |
| JP | 2005287599 A | 10/2005 | |
| JP | 2006167173 A | 6/2006 | |
| JP | 2006254619 A | 9/2006 | |
| JP | 2007002885 A | 1/2007 | |
| JP | 2007043821 A | 2/2007 | |
| JP | 2007089972 A | 4/2007 | |
| JP | 2007089974 A | 4/2007 | |
| JP | 2007215292 A | 8/2007 | |
| JP | 2007247489 A | 9/2007 | |
| JP | 2008011611 A | 1/2008 | |
| JP | 2008099453 A | 4/2008 | |
| JP | 2008104278 A | 5/2008 | |
| JP | 2008132131 A | 6/2008 | |
| JP | 2008193838 A | 8/2008 | |
| JP | 2008297997 A | 12/2008 | |
| JP | 2008301634 A | 12/2008 | |
| JP | 2010133381 A | 6/2010 | |
| JP | 2010136863 A | 6/2010 | |
| JP | 2010203398 A | 9/2010 | |
| JP | 2010209691 A | 9/2010 | |
| JP | 2010261394 A | 11/2010 | |
| JP | 2011169166 A | 9/2011 | |
| JP | 2012021413 A | 2/2012 | |
| JP | 2012062790 A | 3/2012 | |
| JP | 5171953 B2 | 3/2013 | |
| JP | 5572832 B2 | 8/2014 | |
| JP | 5656835 B2 | 1/2015 | |
| JP | 2018507349 A | 3/2018 | |
| WO | 9307388 A1 | 4/1993 | |
| WO | 9414226 A1 | 6/1994 | |
| WO | 9631934 A1 | 10/1996 | |
| WO | 9742413 A1 | 11/1997 | |
| WO | 0064509 A1 | 11/2000 | |
| WO | 2004098677 A1 | 11/2004 | |
| WO | 2005011087 A1 | 2/2005 | |
| WO | 2005028000 A1 | 3/2005 | |
| WO | 2005034312 A2 | 4/2005 | |
| WO | 2006053384 A1 | 5/2006 | |
| WO | 2009157408 A1 | 12/2009 | |
| WO | 2010067682 A1 | 6/2010 | |
| WO | 2010101082 A1 | 9/2010 | |
| WO | 2010101107 A1 | 9/2010 | |
| WO | 2011013483 A1 | 2/2011 | |
| WO | 2012036059 A1 | 3/2012 | |
| WO | 2012040544 A1 | 3/2012 | |
| WO | 2012047550 A1 | 4/2012 | |
| WO | 2012132850 A1 | 10/2012 | |
| WO | 2014113533 A1 | 7/2014 | |
| WO | 2014116676 A1 | 7/2014 | |
| WO | 2014133942 A1 | 9/2014 | |
| WO | 2014179271 A2 | 11/2014 | |
| WO | 2016033131 A1 | 3/2016 | |
| WO | 2016033133 A1 | 3/2016 | |
| WO | 2016130846 A1 | 8/2016 | |
| WO | 2016130944 A1 | 8/2016 | |
| WO | 2016130955 A1 | 8/2016 | |
| WO | 2016130989 A1 | 8/2016 | |

OTHER PUBLICATIONS

Asama et al., "A New Design for a Compact Centrifugal Blood Pump with a Magnetically Levitated Rotor", Asaio Journal, vol. 50, No. 6, Nov. 1, 2004, pp. 550-556.

Asama et al., "Suspension Performance of a Two-Axis Actively Regulated Consequent-Pole Bearingless Motor", IEEE Transactions on Energy Conversion, vol. 28, No. 4, Dec. 2013, pp. 894-901.

Gieras et al., "Advancements in Electric Machines", Nov. 14, 2008, pp. 43-48.

Kosaka et al., "Operating Point Control System for a Continuous Flow Artificial Heart: In Vitro Study", ASAIO Journal, vol. 49, No. 3, May 1, 2003, pp. 259-264.

Neethu et al., "Novel Design Optimization and Realization of Axial Flux Motor for Implantable Blood Pump", Power Electronics, Drives and Energy Systems (Pedes) & 2010 Power India, 2010 Joint International Conference on, IEEE, Dec. 20, 2010, pp. 1-6.

Sandtner et al., "Electrodynamic Passive Magnetic Bearing with Planar Halbach Arrays", Ninth International Symposium on Magnetic Bearings Lexington, Kentucky, USA., Available online at: http://www.silphenix.ch/lexington.pdf, Aug. 3-6, 2004, pp. 1-6.

(56)                    References Cited

OTHER PUBLICATIONS

Terumo Heart, Inc., "Handled With Care—Significantly Reduce the Risk of Cell Damage", Terumo Brochure, Apr. 2010, 2 pages.
Yamazaki et al., "Development of a Miniature Intraventricular Axial Flow Blood Pump", Journal of American Society for Artificial Internal Organs, vol. 39, No. 3, Jul.-Sep. 1993, pp. M224-M230.

* cited by examiner

Operate pump with impeller at a first position — S1

Trigger to move impeller — S2

Operate pump with impeller at a second position — S3

100

101

ALTERNATING PUMP GAPS

CROSS-REFERENCE TO RELATED APPLICATIONS

The present application is a Continuation of U.S. patent application Ser. No. 18/241,433 filed Sep. 1, 2023 (Allowed); which is a Continuation of U.S. patent application Ser. No. 17/240,204 filed Apr. 26, 2021 (now U.S. Pat. No. 11,781,551); which is a Continuation of Ser. No. 16/443,471 filed on Jun. 17, 2019 (now U.S. Pat. No. 11,015,605); which is a Continuation of U.S. patent application Ser. No. 15/041,987 filed Feb. 11, 2016 (now U.S. Pat. No. 10,371, 152); which claims the benefit of U.S. Provisional Appln. No. 62/115,318 filed Feb. 12, 2015, the disclosures which are incorporated herein by reference in their entirety for all purposes.

BACKGROUND OF THE INVENTION

The present invention relates in general to pumping devices, and more specifically, to improved blood pumps with levitated impellers and methods for their control.

Mechanical circulatory support (MCS) devices are commonly used for treating patients with heart failure. One exemplary type of MCS device is a centrifugal flow blood pump. Many types of circulatory support devices are available for either short term or long term support for patients having cardiovascular disease. For example, a heart pump system known as a left ventricular assist device (LVAD) can provide long term patient support with an implantable pump associated with an externally-worn pump control unit and batteries. The LVAD improves circulation throughout the body by assisting the left side of the heart in pumping blood. Examples of LVAD systems are the DuraHeart® LVAS system made by Terumo Heart, Inc. of Ann Arbor, Michigan and the HeartMate II™ and HeartMate III™ systems made by Thoratec Corporation of Pleasanton, California. These systems typically employ a centrifugal pump with a magnetically levitated impeller to pump blood from the left ventricle to the aorta. The impeller is formed as the rotor of the electric motor and rotated by the rotating magnetic field from a multiphase stator such as a brushless DC motor (BLDC). The impeller is rotated to provide sufficient blood flow through the pump to the patient's systemic circulation.

Early LVAD systems utilized mechanical bearings such as ball-and-cup bearings. More recent LVADs employ non-contact bearings which levitate the impeller using hydrodynamic and/or magnetic forces. In one example, the impeller is levitated by the combination of hydrodynamic and passive magnetic forces.

There is a trend for making blood pumps more miniaturized to treat a broader patient population, more reliable, and with improved outcomes. To follow this trend, contactless impeller suspension technology has been developed in several pump designs. The principle of this technology is to levitate the pump impeller using one or a combination of forces from electromagnets, hydrodynamics, and permanent magnets. In the meanwhile, the pump should be hemocompatible to minimize the blood cell damage and blood clot formation. To that end, the bearing gap between the levitated impeller and the pump housing becomes an important factor. A small gap may lead to the high probability of the thrombus formation in the bearing or to elevated hemolysis due to excessive shear stress. Likewise, a large gap can compromise the hydrodynamic bearing performance and the pump efficiency.

One pump design utilizing active magnetic bearings achieves the desired bearing gap by levitating the impeller using magnetic fields generated by electromagnetic coils. However, in such a design there is the need for a separate bearing control system that includes the position sensors and electromagnetic coils to control the impeller position.

Another pump design levitates the impeller using hydrodynamic thrust bearings alone or combined with passive magnetic bearings. However, such a design usually requires a small bearing gap to provide sufficient hydrodynamic bearing stiffness to maintain impeller levitation and prevent contacts between impeller and the pump housing. Such a small gap may result in an insufficient washout and vulnerability to blood clotting thus compromising hemocompatibility.

Pumps utilizing hydrodynamic bearings to suspend the impeller are generally designed to maintain a generally constant gap through all operating conditions. A drawback of such designs is that the impeller starts to tilt when the pump flow rate increases. This impeller position shift under low pressure conditions across the narrow gap creates blood flow stasis, which in turn leads to thrombus formation on the bearing surfaces. One solution to solve the problem is to add a passive magnetic bearing to try to maintain a stable gap. However, the magnetic bearing solution increases the size of the pump and complexity of the system.

What is needed is a pump that addresses these and other problems of known designs. What is needed is a pump with a relatively small form factor and improved outcomes. What is needed is a pump that employs a simple bearing system and enhances blood flow gaps to reduce the risk of thrombus. What is needed is a solution to enhance the bearing gap to achieve adequate washout without increasing the complexity of the pump mechanical design or reducing the pump efficiency.

BRIEF SUMMARY OF THE INVENTION

In summary, various aspects of the present invention are directed to a blood pump system including a pump housing; an impeller for rotating in a pump chamber within the housing; a stator comprising drive coils for applying a torque to the impeller; a bearing mechanism for suspending the impeller within the pump chamber; and a position control mechanism.

Various aspects of the invention are directed to a blood pump system including a pump housing; an impeller for rotating in a pump chamber within the housing; a stator comprising drive coils for applying a torque to the impeller; a first bearing for fixing the impeller relative to a first end of the pump chamber, a first blood gap defined between the impeller and a first bearing surface; a second bearing for fixing the impeller relative to a second end of the pump chamber, a second blood gap defined between the impeller and a second bearing surface; and a position control mechanism.

In various embodiments, the position control mechanism is configured to alternate the pump secondary flow gaps. In various embodiments, the position control mechanism is configured to move the impeller in an axial direction within the pump chamber to adjust a blood gap distance between the impeller and an opposing wall of the housing. In various embodiments, the position control mechanism is configured to move the impeller in an axial direction within the pump chamber to increase the first blood gap thereby increasing a washout rate.

In various embodiments, the washout rate is the average washout rate during a respective period of time. In various embodiments, the washout rate is the peak washout rate during a respective period of time. For example, the respective period of time may be the period during which the impeller is moved to a target position to increase the washout rate.

In various embodiments, the position control mechanism is configured to move the impeller periodically and intermittently. The position control mechanism may be configured to move the impeller for at least several seconds every minute. The position control mechanism may be configured to move the impeller based on a triggering event. The position control mechanism may be configured to move the impeller based on the impeller crossing a speed threshold. The speed threshold may be a low speed threshold. The triggering event may be based on a low speed threshold and time threshold.

In various embodiments, the pump is configured with at least a first balanced position with a narrow first gap and a second balanced position with a narrow second gap. The impeller may be controlled such that the impeller spends substantially equal amounts of time in the first and second balanced positions. In various embodiments, the amount of time the impeller spends in each balanced position is inversely proportional to the gap size. In various embodiments, one of the gaps is identified as being prone to stasis and the impeller spends more time in a position away from the identified gap.

In various embodiments, the movement of the impeller is asynchronous with the native heartbeat. In various embodiments, the movement of the impeller is synchronous with the native heartbeat.

In various embodiments, a total blood gap under normal operating conditions is 50 micrometers. In various embodiments, a total blood gap under normal operating conditions is 100 micrometers. In various embodiments, a total blood gap under normal operating conditions is 200 micrometers. In various embodiments, a total blood gap under normal operating conditions is 1000 micrometers. In various embodiments, a total blood gap under normal operating conditions is 2000 micrometers. In various embodiments, the impeller is moved to a position to decrease a respective blood gap by about 20%, by about 30%, by about 40%, by about 50%, by about 60%, by about 70%, by about 75%, by about 80%, or by about 90%.

Various aspects of the invention are directed to a method of operating a pump as described in any of the preceding paragraphs.

Various aspects of the invention are directed to a method of operating a blood pump including a housing and an impeller for rotating within a pump chamber within the housing including rotating the impeller within the pump chamber, the impeller being suspended within the pump chamber by a first bearing at a first end of the pump chamber and a second bearing at a second end of the pump chamber; and moving the impeller in an axial direction within the pump chamber to increase a first blood gap defined by the first bearing and to decrease a second blood gap defined by the second bearing.

Various aspects of the invention are directed to at least one system, method, or computer-program product as described in the specification and/or shown in any of the drawings.

In one aspect, a blood pump system is provided. The pump system may include a pump housing and an impeller for rotating in a pump chamber within the housing. The impeller may have a first side and a second side opposite the first side. The pump system may also include a stator having drive coils for applying a torque to the impeller and at least one bearing mechanism for suspending the impeller within the pump chamber. The pump system may further include a position control mechanism for moving the impeller in an axial direction within the pump chamber to adjust a size of a first gap and a size of a second gap, thereby controlling a washout rate at each of the first gap and the second gap. The first gap may be defined by a distance between the first side and the housing and the second gap is defined by a distance between the second side and the pump housing.

In another aspect, a blood pump system may include a pump housing, an impeller for rotating in a pump chamber within the housing, and a stator having drive coils for applying a torque to the impeller. The pump system may also include a first bearing for fixing the impeller relative to a first end of the pump chamber. A first blood gap may be defined between the impeller and a first bearing surface. The pump system may further include a second bearing for fixing the impeller relative to a second end of the pump chamber. A second blood gap may be defined between the impeller and a second bearing surface. The pump system may include a position control mechanism for moving the impeller in an axial direction within the pump chamber to increase the first blood gap thereby increasing a washout rate at the first blood gap.

In another aspect, a method is provided of operating a blood pump including a housing and an impeller for rotating within a pump chamber within the housing. The method may include rotating the impeller within the pump chamber. The impeller may be suspended within the pump chamber by a first bearing at a first end of the pump chamber and a second bearing at a second end of the pump chamber. The method may also include moving the impeller in an axial direction within the pump chamber to increase a first blood gap defined by the first bearing and to decrease a second blood gap defined by the second bearing.

The structures and methods of the present invention have other features and advantages which will be apparent from or are set forth in more detail in the accompanying drawings, which are incorporated in and form a part of this specification, and the following Detailed Description of the Invention, which together serve to explain the principles of the present invention.

DETAILED DESCRIPTION OF THE INVENTION

Figure 1:
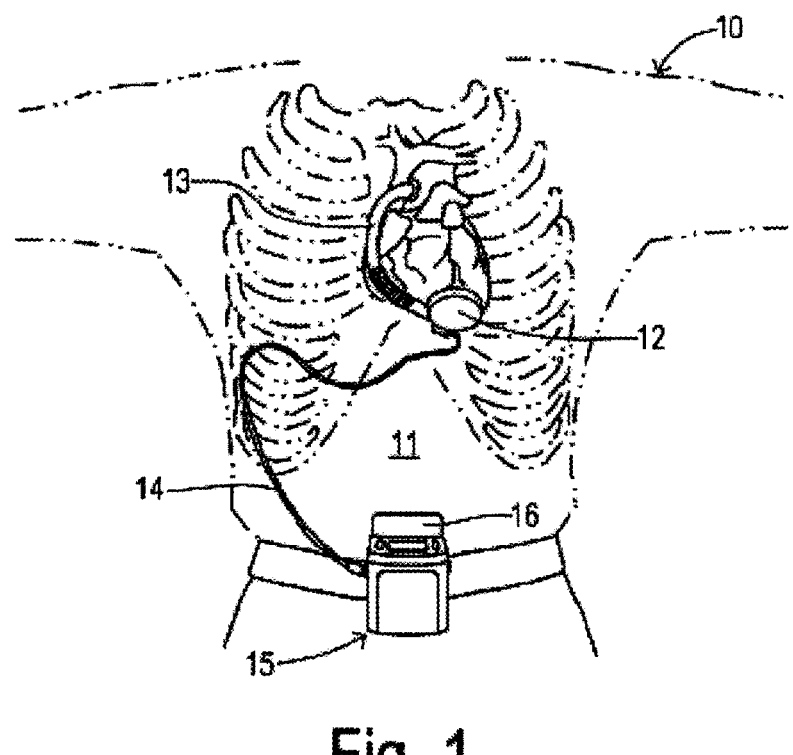
FIG. 1 is a diagram of an implantable pump as one example of a rotary machine employing the present invention.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

For convenience in explanation and accurate definition in the appended claims, the terms "up" or "upper", "down" or "lower", "inside" and "outside" are used to describe features of the present invention with reference to the positions of such features as displayed in the figures.

In many respects the modifications of the various figures resemble those of preceding modifications and the same reference numerals followed by subscripts "a", "b", "c", and "d" designate corresponding parts.

As used herein, "gap" generally refers to the secondary flow gaps around the impeller as would be understood by one of skill in the art. The primary flow is through the impeller blade regions. The secondary flow gaps are the other areas of fluid, generally around the impeller. In some respects, the secondary flow gaps are between the impeller and the housing wall and define the hydrodynamic bearing.

The term "machine-readable medium" includes, but is not limited to, portable or fixed storage devices, optical storage devices, wireless channels and various other mediums capable of storing, containing or carrying instructions and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. One or more processors may perform the necessary tasks.

Although aspects of the invention will be described with reference to a blood pump, one will appreciate that the invention can be applied to other types of pumps. The mechanisms and methods of the invention will be described in relation to blood pumps and in particular the ability to adjust the impeller operating position to address performance, such as the attendant risks for thrombus and hemolysis when pumping blood. One will appreciate from the description herein that the invention can be applied broadly to other pumps, rotary machines, and induction motors.

Turning to the drawings, aspects of the invention enable to the ability to enhance or control the bearing gaps. One might wish to increase the bearing gap to adjust the washout rate, lubricate the bearing surfaces, or remove materials (particulates, thrombus, etc.) from the bearing gap. Another use of the invention may be to increase pump efficiency. As is known in the art, the motor efficiency increases as the impeller magnet moves closer to the motor drive coils. Another use of the invention may be to correct impeller malpositioning due to bulk forces or external forces (e.g., bumps or movements of the patient's body). These and other advantages can be achieved without the need for complex control systems in accordance with the invention.

Various aspects of the invention are directed to improving the washout in a respective pump bearing gap by moving the impeller to a position to increase the respective gap size. The impeller may be moved periodically (e.g., by time) or triggered by an event. When the impeller moves up, the larger gap on the bottom of the pump leads to a higher flow rate, which in turn leads to a higher washout rate. The upward movement of the impeller may also "squeeze" the blood above the impeller in a sort of pumping action, which also increases the washout rate. The fluid above is squeezed as the impeller moves, but once the impeller is in the new position the pumping effect is lost whereas the higher washout rate still remains below at the larger gap. In other words, the pumping effect on washout rate occurs at a specific point in time whereas the larger gap effect is temporal in nature. The basic concept makes use of the fact that the gap size is correlated to the washout rate. The washout rate relates to an average time for a full exchange of fluid. Accordingly, if the gap size divided by the washout rate is equal to a few seconds that doesn't necessarily mean the impeller should move for only a few seconds. Oftentimes, the impeller is moved for between about 100%, 120%, 150%, 200%, or other percentage of the average time for full exchange calculated by the gap size divided by the washout rate to have higher confidence. The washout flow rate is generally proportional to the cube of the gap width. Therefore, theoretically the total washout flow rate will be 8 times greater when the gap becomes 2 times wider. See W. K. Chan et al., Analytical Investigation of Leakage Flow I Disk Clearance of Magnetic Suspended Centrifugal Impeller, Artificial Organ (2000). Washout rate is vital, as a failure to get full washout may result in thrombosis formation in areas of stasis or where fluid isn't exchanged. This creates two risks: 1) the thrombus may dislodge and flow into the body, thus causing an embolism (or a stroke depending on where it goes), and 2) the thrombus may continue unabated, causing the activated site to form more platelets, which in turn provide a site for thrombin to adhere.

Accordingly, alternating the gaps has been found to improve the hydrodynamic bearing washout while maintaining a small total gap (good pump efficiency, proper HD bearing operations, etc.). In other words, alternating the gaps improves the washout without increasing the total gap.

The above technique can be implemented in a pump with a hydrodynamic and/or electromagnetic bearing. With a hydrodynamic bearing design, it is expected that there will be power loss associated with movement of the impeller. In one embodiment using electromagnets and hydrodynamic pressure grooves, the power loss can be minimized by designing the bearing stiffness curve to have at least two stable (eccentric) positions and facilitating movement of the impeller between these at least two positions. In one example, the electromagnets need additional force only to move the impeller from one side to another, and no such force is required to keep the impeller on one side.

In one embodiment, an electromagnetic force control method is used to change the impeller position and enhance the effective gap between the impeller and the blood chamber. The technique uses the same pump motor stator coils adjust the impeller position as is used to apply a torque to the impeller. No additional control subsystems and components are necessary.

Turning now to the drawings, wherein like components are designated by like reference numerals throughout the various figures, attention is directed to FIG. 1 which depicts an exemplary pump implanted in a heart failure patient.

A typical cardiac assist system includes a pumping unit, drive electronics, microprocessor control unit, and an energy source such as rechargeable batteries and/or an AC power conditioning circuit. The system is implanted during a surgical procedure in which a centrifugal pump is placed in the patient's chest. An inflow conduit is pierced into the left ventricle to supply blood to the pump. One end of an outflow conduit is mechanically fitted to the pump outlet and the other end is surgically attached to the patient's aorta by anastomosis. A percutaneous cable connects to the pump, exits the patient through an incision, and connects to the external control unit.

Various aspects of the implantable pump are similar to those shown and described in U.S. Pat. Nos. 4,528,485; 4,857,781; 5,229,693; 5,588,812; 5,708,346; 5,917,297; 6,100,618; 6,222,290; 6,249,067; 6,268,675; 6,355,998; 6,351,048; 6,365,996; 6,522,093; 7,972,122; 8,686,674; 9,265,870; and 9,371,826, the entire contents which are incorporated herein by reference for all purposes.

The exemplary system utilizes an implantable pump with contactless bearings for supporting the impeller. Contactless bearings (i.e., levitation) provide a number of potential benefits. Because they reduce rotational friction, theoretically they improve motor efficiency and reduce the risk of introducing particulates into the fluid. In one example, the impeller employs upper and lower plates having magnetic materials (the terminology of upper and lower being arbitrary since the pump can be operated in any orientation). A stationary magnetic field from the upper side of the pump housing attracts the upper plate and a rotating magnetic field from the lower side of the pump housing attracts the lower plate. The forces cooperate so that the impeller rotates at a levitated position within the pumping chamber. Features (not shown) may also be formed in the walls of the pumping chamber to produce a hydrodynamic bearing wherein forces from the circulating fluid also tend to center the impeller. Hydrodynamic pressure grooves adapted to provide such a hydrodynamic bearing are shown in U.S. Pat. No. 7,470,246 issued Dec. 30, 2008, titled "Centrifugal Blood Pump Apparatus," which is incorporated herein for all purposes by reference.

The exemplary impeller has an optimal location within the pumping chamber with a predetermined spacing from the chamber walls on each side. Maintaining a proper spacing limits the shear stress and the flow stasis of the pump. A high shear stress can cause hemolysis of the blood (i.e., damage to cells). Flow stasis can cause thrombosis (i.e., blood clotting).

With continued reference to FIG. 1, a patient is shown in fragmentary front elevational view. Surgically implanted either into the patient's abdominal cavity or pericardium 11 is the pumping unit 12 of a ventricular assist device. An inflow conduit (on the hidden side of unit 12) pierces the apex of the heart to convey blood from the patient's left ventricle into pumping unit 12. An outflow conduit 13 conveys blood from pumping unit 12 to the patient's ascending aorta. A percutaneous power cable 14 extends from pumping unit 12 outwardly of the patient's body via an incision to a compact control unit 15 worn by patient 10. Control unit 15 is powered by a main battery pack 16 and/or an external AC power supply, and an internal backup battery. Control unit 15 includes a commutator circuit for driving a motor within pumping unit 12.

In various embodiments, the commutator circuit and/or various electronics may be on the implanted side of the system. For example, various electronics may be positioned on-board the pump or in a separate hermetically sealed housing. Among the potential advantages of implanting electronics is the ability to control the pump even when communication is lost with the control unit 15 outside the body.

Figure 2:
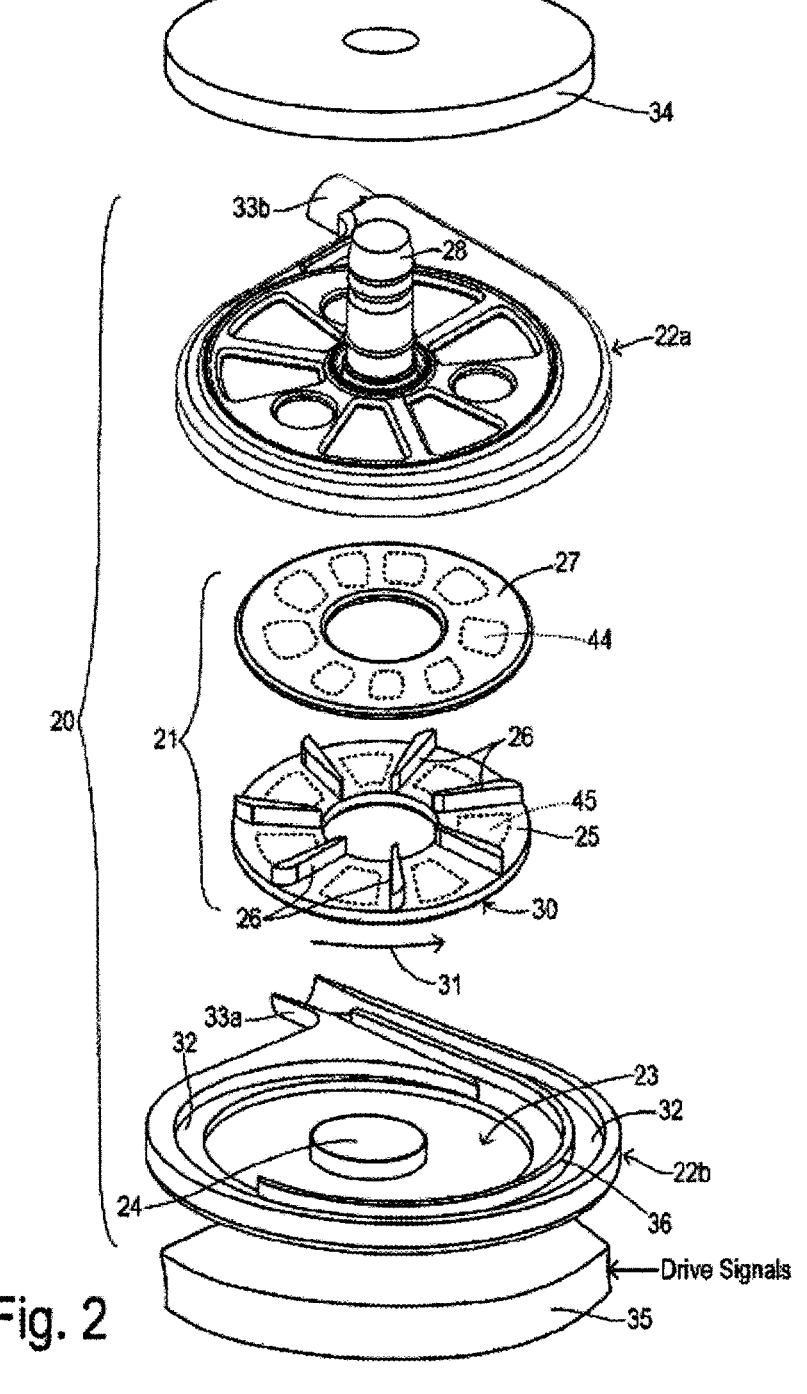
FIG. 2 is an exploded, perspective view of the exemplary centrifugal pump of FIG. 1.
Figure 3:
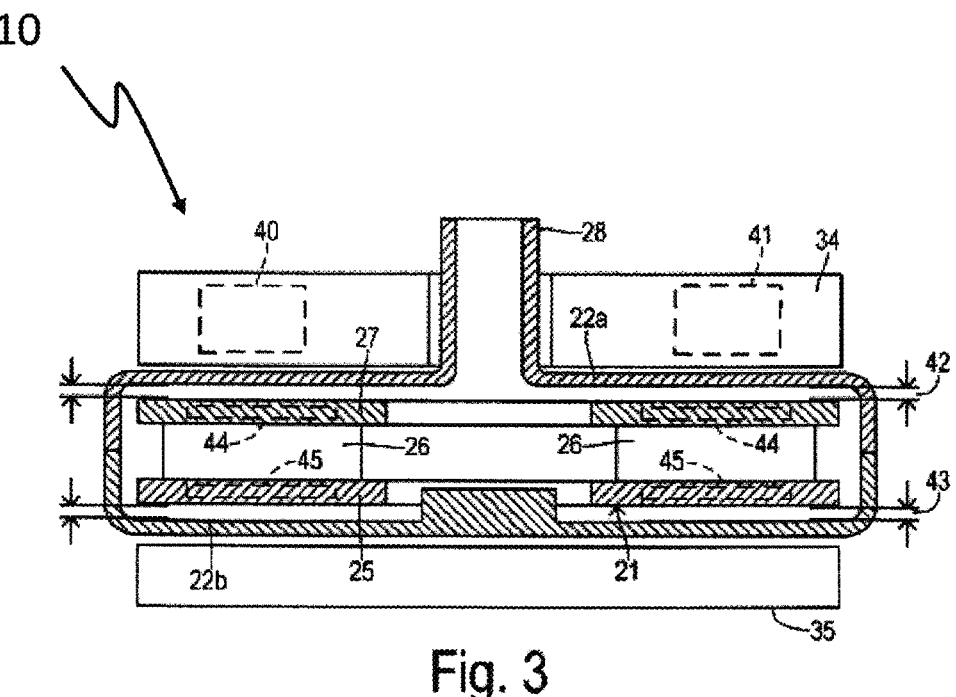
FIG. 3 is a cross-sectional view of the exemplary pump of FIG. 1, illustrating the impeller levitated at a first balanced position generally centered within the pumping chamber in accordance with aspects of the invention.

FIGS. 2 and 3 show exemplary centrifugal pumping devices in accordance with various aspects of the invention. The exemplary pumping device includes an impeller position controller to modify or select a position for the impeller. As will be described in further detail below, the impeller is positioned with a fixed pump chamber such that movement causing one pump gap to decrease generally causes the other pump gap to increase, and vice versa.

FIG. 2 shows exemplary centrifugal pump unit 20 used in the system of FIG. 1. The pump unit 20 includes an impeller 21 and a pump housing having upper and lower halves 22a and 22b. Impeller 21 is disposed within a pumping chamber 23 over a hub 24. Impeller 21 includes a first plate or disc 25 and a second plate or disc 27 sandwiched over a plurality of vanes 26. Second disc 27 includes a plurality of embedded magnet segments 44 for interacting with a levitating magnetic field created by levitation magnet structure 34 disposed against housing 22a. For achieving a small size, magnet structure 34 may comprise one or more permanent magnet segments providing a symmetrical, static levitation magnetic field around a 360° circumference. First disc 25 also contains embedded magnet segments 45 for magnetically coupling with a magnetic field from a stator assembly 35 disposed against housing 22b. Housing 22a includes an inlet 28 for receiving blood from a patient's ventricle and distributing it to vanes 26. Impeller 21 is preferably circular and has an outer circumferential edge 30. By rotatably driving impeller 21 in a pumping direction 31, the blood received at an inner edge of impeller 21 is carried to outer circumferential 30 and enters a volute region 32 within pumping chamber 23 at an increased pressure. The pressurized blood flows out from an outlet 33 formed by housing features 33a and 33b. A flow-dividing guide wall 36 may be provided within volute region 32 to help stabilize the overall flow and the forces acting on impeller 21.

FIG. 3 shows impeller 21 located in a balanced position. In the exemplary embodiment, the balanced position is at or near the center of the pump chamber. In the balanced position, the forces acting on the impeller are generally balanced to stabilize the impeller. The balanced position sometimes refers to the position the impeller naturally stabilizes or finds equilibrium during operation.

As one will understand from the description above, however, the balanced position is not necessarily a specific, static location. The hydrodynamic forces on the impeller will change as the rotational speed of the impeller changes. In turn, the magnetic attractive forces on the impeller will change as the impeller moves closer to or away from the magnet structure 34 and stator assembly 35. Accordingly, the impeller generally finds a new balanced position as the rotational speed changes. As will be described below, however, aspects of the invention are directed to moving the impeller or changing the balanced position for each given rotational speed. For example, the impeller position control mechanisms to be described facilitate moving the impeller axially (up or down) without changing the rotational speed and all other. This has the effect of enabling movement of the impeller independent of rotor speed. An advantage of this technique is that rotor speed can be determined in normal course (e.g., by a physician based on the patient's physiological needs) without concern for changing the impeller position. Conversely, the impeller position can be changed without affecting pumping throughput.

FIG. 3 shows impeller 21 located at or near a centered position wherein disc 27 is spaced from housing 22A by a gap 42 and impeller disc 25 is spaced from housing 22B by a gap 43. In the exemplary embodiment, the center position is chosen as the balanced or eccentric point to ensure substantially uniform flow through gap 42 and gap 43. During pump operation, the balanced position is maintained by the interaction of (a) attractive magnetic forces between permanent magnets 40 and 41 in levitation magnet structure 34 with imbedded magnetic material 44 within impeller disc 27, (b) attractive magnetic forces between stator assembly 35 and embedded magnet material 45 in impeller disc 25, and (c) hydrodynamic bearing forces exerted by the circulating fluid which may be increased by forming hydrodynamic pressure grooves in housing 22 (not shown). By using permanent magnets in structure 34 a compact shape is realized and potential failures associated with the complexities of implementing active levitation magnet control are avoided. To properly balance impeller 21 at the centered position, however, and because other forces acting on impeller 21 are not constant, an active positioning control is still needed. In particular, the hydrodynamic forces acting on impeller 21 vary according to the rotational speed of impeller 21. Furthermore, the attractive force applied to impeller 21 by stator assembly 35 depends on the magnitude of the magnetic field and the angle by which the magnetic field leads the impellers magnetic field position. In one embodiment, the attractive force is created by a direct current ($I_d$) as will be described in more detail below.

In one embodiment, the impeller position is controlled using vector motor control. Several structures and techniques for modifying impeller position using vector motor control will now be described with reference to FIGS. 3 to 7.

Figure 4A:
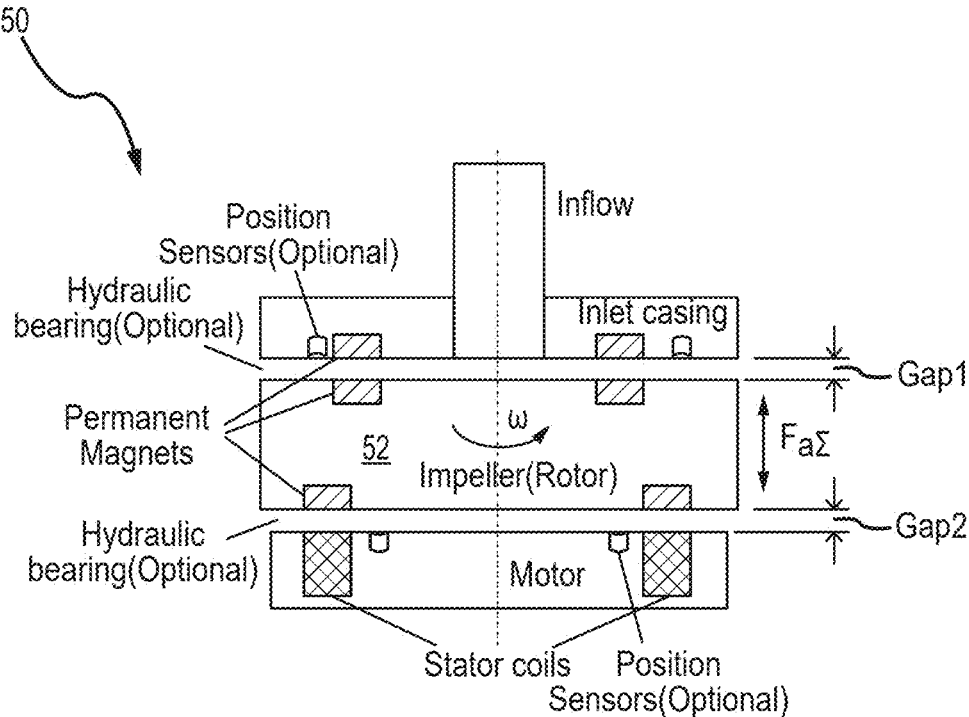
FIG. 4a is a schematic view of the exemplary pump of FIG. 1, illustrating the impeller levitated eccentrically in the pump chamber by the main bearing components.

FIG. 4a shows the main structure of an exemplary centrifugal pump 50 similar to that shown in FIG. 3. It is understood that other pump configurations may be employed, including various combinations of permanent magnets, motor stator windings, and hydrodynamic bearings. In the exemplary embodiment, the rotor is formed as an impeller and driven by a motor. The impeller is also levitated by the combined force $F_{a\Sigma}$, which can be expressed as the following equation:

$$F_{a\Sigma} = F_{hdb} + F_{pm} + F_{em}$$

Where, $F_{a\Sigma}$ is the combined force to levitate the impeller $F_{hdb}$ is the combination of hydrodynamic forces from the inlet side bearing, the motor side bearing, or both $F_{pm}$ is the combination of permanent magnet attraction forces $F_{em}$ is the magnetic attraction force generated from the motor.

When the impeller is stabilized, $F_{a\Sigma}$ should be equal to zero. Usually $F_{em}$ can be controlled through the electronic system to adjust the impeller position since all the others are the fixed configurations as the passive mode. Therefore, the basic design concept of this invention is to apply the motor vector control (FOC) to control the force $F_{em}$ so that the impeller position can be adjusted while rotating only using one set of motor coil and drive system. In such way, there is no additional cost in the pump structure.

Figure 4C:
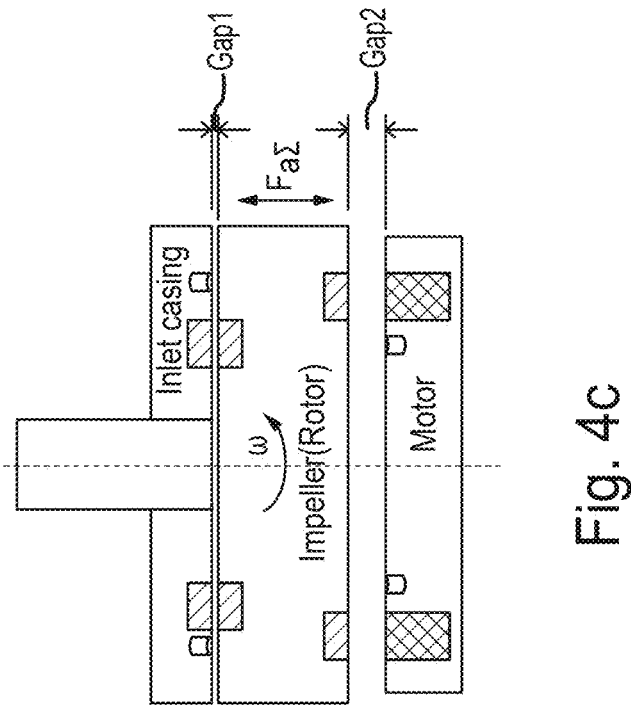
FIG. 4c is a schematic view of the pump of FIG. 1, illustrating the impeller moved to yet another eccentric position at the top of the pump chamber.
Figure 4B:
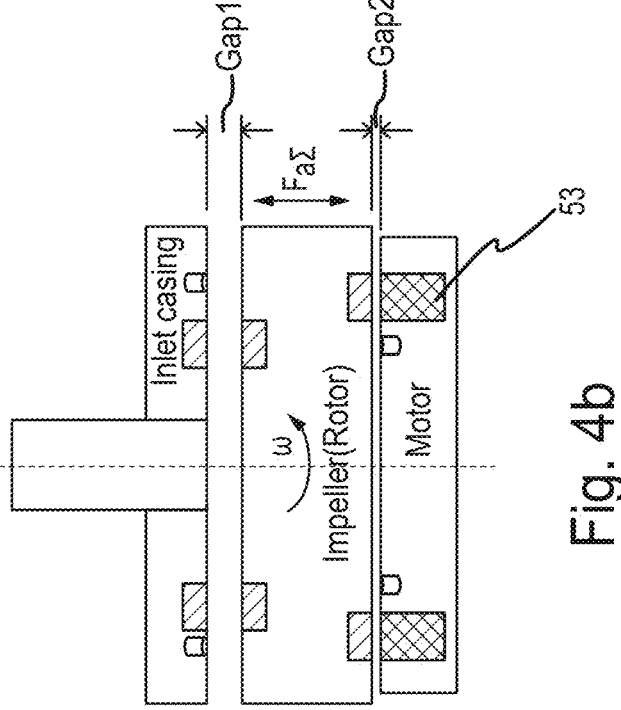
FIG. 4b is a schematic view of the pump of FIG. 1, illustrating the impeller moved to another eccentric position at the bottom of the pump chamber.

FIGS. 4a, 4b, and 4c illustrate a pump in accordance with various aspects of the invention. FIG. 4a illustrates an exemplary pump 50 with an impeller 52 in a pump chamber. Pump 50 is configured similar to pump 10 in FIG. 3. FIGS. 4b and 4c illustrate the same pump 50 in FIG. 4a except with the impeller moved down and up, respectively, in accordance with the invention. In FIG. 4b, the impeller 52 is in a lowered position such that Gap 2 is smaller and Gap 1 is commensurately wider. In this position the washout rate across Gap 1 is exponentially higher relative to FIG. 4a. In FIG. 4c, the impeller 52 is in a raised position such that Gap 2 is wider and Gap 1 is commensurately narrower. In this position, the washout rate in Gap 2 is exponentially higher relative to FIG. 4a.

In various respects, the washout rate refers to the average washout rate during a respective period of time. In various respects, the washout rate refers to the peak washout rate. The respective period of time may be any designated period of time, for example, the period during which the impeller is moved to a target position to increase the washout rate.

Figure 5:
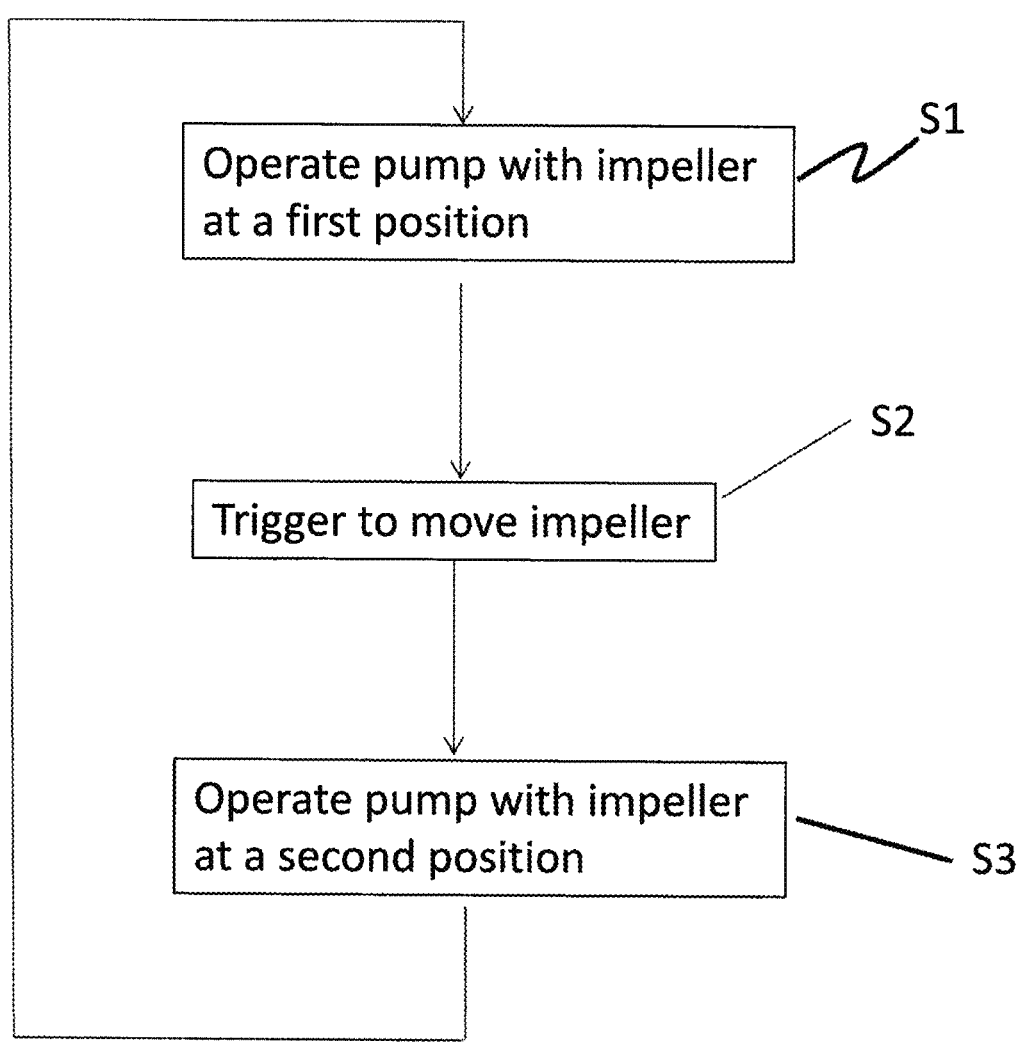
FIG. 5 is a flowchart showing a method of controlling impeller position in accordance with the invention.

FIG. 5 illustrates an exemplary simplified method for controlling the pump. In step S1, the pump is operated with the impeller at a first balanced position. In step S2, a trigger is identified. In response, the impeller is moved to a second position in step S3. Thereafter the impeller eventually moves back to the first position.

The trigger may be temporal-based or event-based. In various embodiments, the position control mechanism is configured to move the impeller periodically and intermittently. In other words, the trigger can be the passage of a predetermined amount of time and/or based on a set frequency and cycle. In one example, the position control mechanism is configured to move the impeller for at least several seconds every minute. In various embodiments, the position control mechanism is configured to move the impeller based on the impeller crossing a speed threshold. The speed threshold may be a low speed threshold. The trigger may be based on a low speed threshold and time threshold. For example, the impeller may be moved after it spends more than a set amount of time at a low speed. This may be beneficial because low speeds can lead to touchdown events, stasis, and other issues. Thus, the impeller may be moved to ensure any particulates or thrombus are cleared from the gap.

In various embodiments, the pump is configured with at least a first balanced position with a narrow first gap and a second balanced position with a narrow second gap. As compared to FIG. 4*a*, FIG. 4*b* shows the impeller defining a narrow Gap 2 and FIG. 4*c* shows the impeller defining a narrow Gap 1. Because the pump chamber dimensions are fixed and the total gap is likewise fixed, Gap 1 increases by the same distance that Gap 2 decreases. In FIG. 4*c*, the impeller has moved upward to a third balanced position such that Gap 1 has decreased and Gap 2 has increased by a commensurate amount.

The impeller may be controlled such that the impeller spends substantially equal amounts of time in the first and second balanced positions. This may be useful where the pump is otherwise designed for the impeller to normally be in a centered position, such as shown in FIG. 4*a*. In various embodiments, the amount of time the impeller spends in each balanced position is inversely proportional to the gap size. This may be useful where the pump is otherwise designed to have uneven gaps. In various embodiments, one of the gaps is identified as being prone to stasis and the impeller spends more time in a position away from the identified gap.

In various embodiments, the movement of the impeller is asynchronous with the native heartbeat. In various embodiments, the movement of the impeller is synchronous with the native heartbeat.

In various embodiments, a total blood gap under normal operating conditions is 50 micrometers. In various embodiments, a total blood gap under normal operating conditions is 100 micrometers. In various embodiments, a total blood gap under normal operating conditions is 200 micrometers. In various embodiments, a total blood gap under normal operating conditions is 1000 micrometers. In various embodiments, a total blood gap under normal operating conditions is 2000 micrometers. In various embodiments, the impeller is moved to a position to decrease a respective blood gap by about 20%, by about 30%, by about 40%, by about 50%, by about 60%, by about 70%, by about 75%, by about 80%, or by about 90%.

One will appreciate that FIGS. 4*a*, 4*b*, and 4*c* are illustrative only. In practice the impeller is freely suspended and not perfectly fixed in a position. Because the exemplary pump suspends the impeller by balancing a combination of passive forces, the impeller actually exhibits a moderate amount of movement in practice. Indeed, the impeller will move up and down depending on the rotational speed at least because of the relationship of rpms to hydrodynamic force. However, for a set rotational speed, the impeller is typically constrained with a defined envelope of space which is referred to her as a "position" for simplicity of explanation.

Mechanical or contact bearings exhibit little to no movement regardless of the rotational speed and other factors. Nonetheless, contact bearings demonstrate some operational movement even if such movement requires precise instruments to be measured. Many types of blood pumps, for example, utilize bearings which are washed and lubricated by an external source. Examples of a pump with a blood-immersed bearing are described in U.S. Pat. Nos. 5,588,812 and 9,265,870, incorporated herein by reference for all purposes. In one example, a pump includes blood immersed contact bearings such as a ball-and-cup. In one example, the bearings are washed and/or lubricated by saline or infusate. The use of saline is a common scenario for percutaneous pumps because they have a fluidic connection to sources outside the body. Examples of percutaneous pumps with contact bearings are disclosed in U.S. Pat. Nos. 7,393,181 and 8,535,211, incorporated herein by reference for all purposes. As will be appreciated by one of skill in the art, contact bearings which are designed to have a fluid at least periodically washing between the contact surface will have some movement. Although this movement is small relative to non-contact bearings (e.g., on the order of 5, 10, 20, 100 or more times smaller), they are subject to some degree of movement.

Conventional thinking is that a blood pump (e.g., left ventricular assist device) should be designed to maintain a stable impeller position and consistent blood gaps across the device lifetime. In blood pumps, in particular, movement of the impeller is often associated with hemolysis and other undesirable risks. There is a belief that decreasing a pump gap creates a region of stasis which leads to thrombus and other adverse events.

However, it has been found that adjusting the pump gap in a controlled and designed manner can actually improve performance and outcomes. Various aspects of the invention are directed to pumps configured to actively and purposefully modify the impeller position. In one embodiment, the balanced position of the impeller is changed during operation.

There are several potential benefits to the technique described above for moving the impeller and alternating the pump gaps. One of these potential benefits is the ability to increase the peak washout flow velocity. Another potential benefit is the ability to prevent or reduce the collection of ingested thrombus in narrow gaps without increasing the total gap size. In turn, pump efficiency and performance are not compromised. Existing solutions (e.g., stable-gap hydrodynamic bearing designs) rely on the native heart to change the blood flow pattern in the narrow gap areas (such as systole/diastole). The inventive technique is advantageous because it actively changes the flow pattern independently of the native heart function, impeller speed, etc. Also, many heart failure patients have weakened native hearts with insufficient pulsatility to actually wash out the bearing gaps. With the inventive technique, the combination of the external pressure change and internal geometry change (rotor position change) will minimize the blood flow stasis which causes pump thrombosis.

Figure 6:
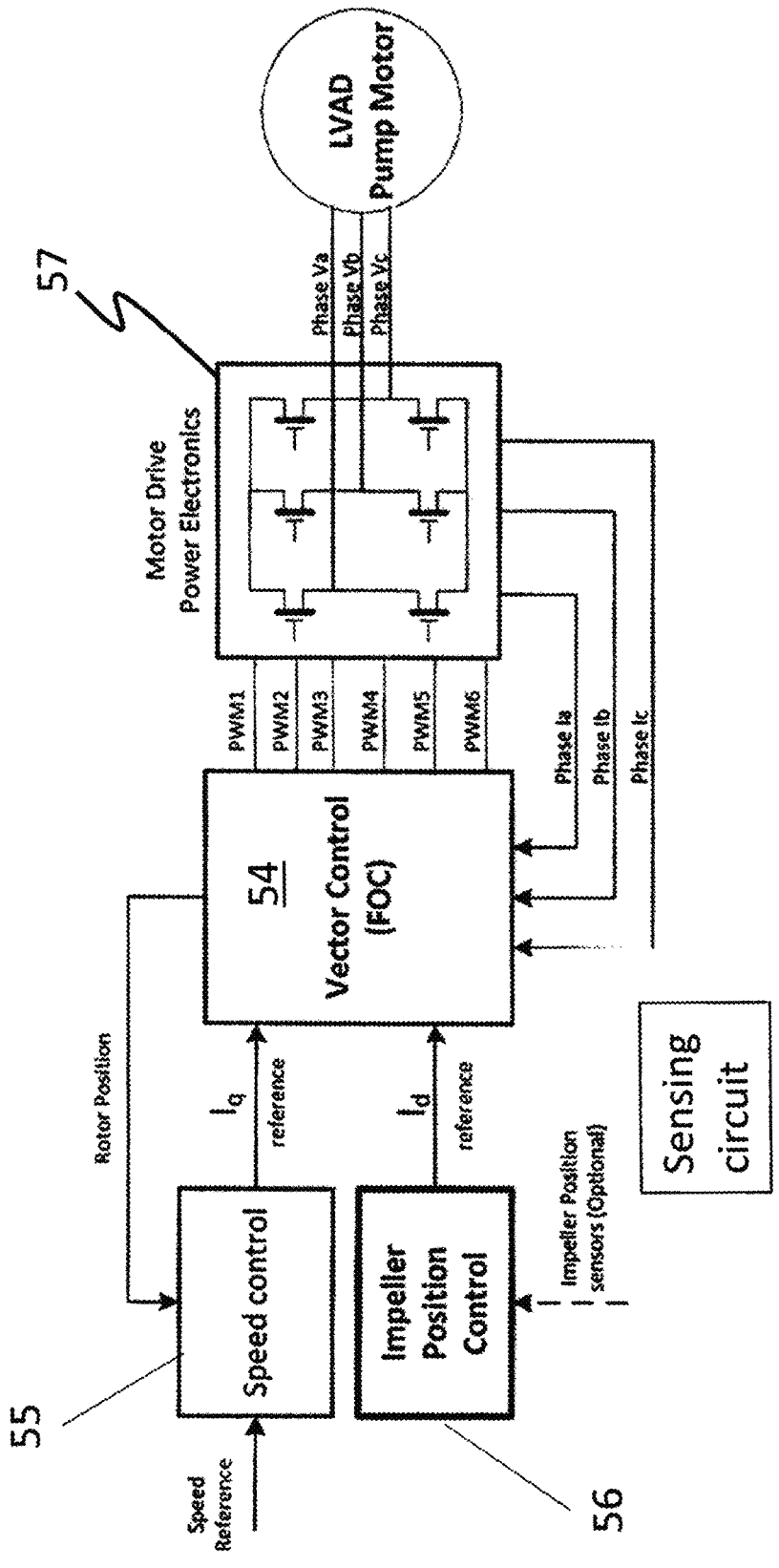
FIG. 6 is a block diagram of a pump control system in accordance with the invention.
Figure 7:
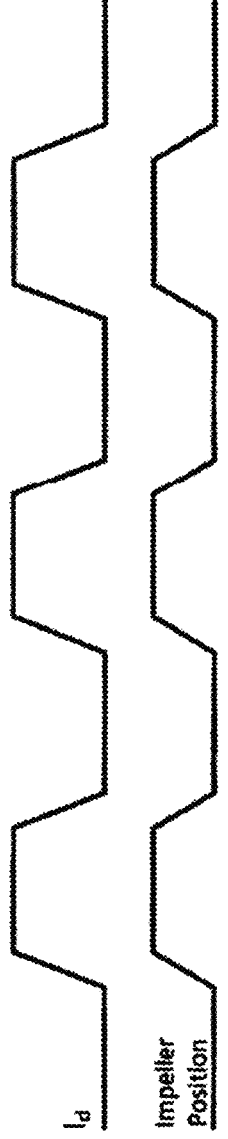
FIG. 7 is a line chart depicting the method of controlling the impeller position in accordance with the invention.
Figure 7:

FIGS. 6 and 7 illustrate an exemplary method for controlling voltages applied to a stator in order to provide a desired rotation for a permanent magnet rotor (e.g., the impeller) 52 using a field oriented control (FOC) algorithm, which is also known as vector control. It is known in FOC that the stator magnetic field should generally lead the impeller position by 90° for maximum torque efficiency. The magnitude of the attractive force on the impeller is proportional to the magnitude of the phase currents in the stator. Phase current is adjusted by the FOC algorithm according to torque demands for the pump.

At any particular combination of the (1) magnitude of the phase current and (2) the speed of the impeller, modifying the $I_d$ current for generating the phase voltages can change the attractive force generated by the stator thereby affecting the impeller balance. In turn, the impeller moves until it settles at a new balanced position where the hydrodynamic forces and magnetic forces are balanced. In this manner, the impeller can be moved simply by adjustments to the motor control signal.

FIGS. 4b, 4c, 5, 6, and 7 illustrate an exemplary system in accordance with aspects of the invention. FIG. 6 is a schematic diagram of pump control system with the proposed impeller position control. Based on the principle of motor vector control, the torque current that is usually called quadrature current ($I_q$ current) and stator coil flux current that is called direct current ($I_d$ current) can be decoupled and controlled independently. The quadrature current $I_q$ current is used to control the impeller rotational speed. The direct $I_d$ current controls the magnetic flux of electromagnetic coils which creates a resulting attractive force on the impeller.

In accordance with the invention, $I_d$ current is utilized to control the impeller position by enhancing or weakening the magnetic flux between impeller (rotor) and motor stator coils to adjust the attraction force $F_{em}$. This in turn changes the impeller position (shown in FIG. 7). In various embodiments, the attractive force is created by adjusting the phase angle using FOC.

In one embodiment, the impeller position control technique is implemented as an open loop control without impeller position sensors. In one embodiment, impeller position control technique is implemented as a closed loop control with impeller position sensors.

In order to ensure proper positioning, active monitoring and control of the impeller position has been employed in the exemplary embodiment by adjusting the stationary magnetic field. However, position sensors and an adjustable magnetic source occupy a significant amount of space and add to the complexity of a system. Accordingly, the use of sensors may depend on the design requirements. Suitable sensors may include, but are not limited to, Hall-effect sensors, variable reluctance sensors, and accelerometers.

In one embodiment using the open loop control, the impeller is controlled by periodically alternating the position from one side to another (e.g., from inlet side to motor side) by modulating the $I_d$ current as shown in FIG. 7. In this manner, the side gaps (Gap 1 and Gap 2) as shown in FIGS. 4b and 4c can be increased or decreased.

With continued reference to FIGS. 6 and 7, the position control technique can be implemented into the hardware and/or software of the system. By example, the controller may employ FOC to supply a multiphase voltage signal to the stator assembly 53. The exemplary stator assembly is a three-phase stator. Individual phases a, b, and c and currents $I_a$, $I_b$, and $I_c$ may be driven by an H-bridge inverter functioning as a commutation circuit driven by a pulse width modulator (PWM) circuit. An optional current sensing circuit associated with the inverter measure instantaneous phase current in at least two phases providing current signals designated $I_a$ and $I_b$. A current calculating block receives the two measured currents and calculates a current $I_c$ corresponding to the third phase. The measured currents are input to Vector Control (FOC) block 54 and to a current observer block (not shown) which estimates the position and speed of the impeller. The impeller position and speed are input to the FOC block from speed control block 55 and position control block 56. A target speed or revolutions per minute (rpm) for operating the pump is provided by a conventional physiological monitor to FOC block 54. The target rpm may be set by a medical caregiver or determined according to an algorithm based on various patient parameters such heartbeat, physiological needs, suction detection, and the like. FOC block 54 and drive electronics 57 generate commanded voltage output values Va, Vb, and Vc. The Va, Vb, and Vc commands may also be coupled to the observer block for use in detecting speed and position.

The exemplary system differs from conventional configurations inasmuch as the FOC block and electronics are configured to alter the field oriented control algorithm so that the $I_d$ current can be varied independently to generated the required attractive force. The exemplary system potentially sacrifices such efficiency in return for other benefits. Among the benefits of the exemplary system is the ability to independently control the impeller position.

Figure 8:
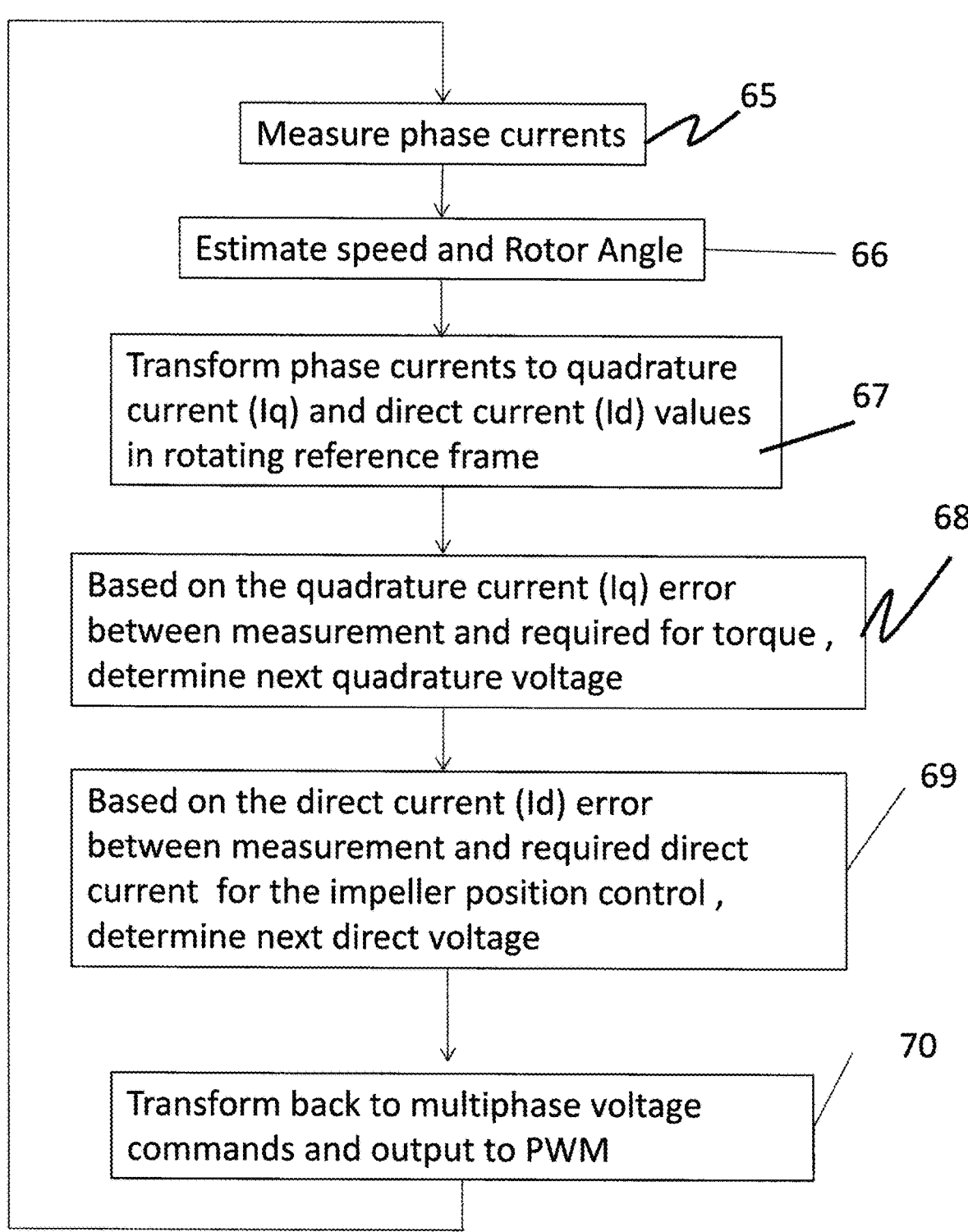
FIG. 8 is a flowchart showing a method of controlling impeller position in accordance with the invention.

FIG. 8 illustrates a method of moving the impeller using a FOC algorithm. In one embodiment, the invention proceeds according to a method as shown in FIG. 8 which highlights a portion of the impeller position control with the field oriented control algorithm. Thus, in step 65 the phase currents are measured. Based on the measured phase currents, the current speed and rotor angle are estimated in step 66 based on the rotor angle determined in step 66. The phase currents are transformed into a two-axis coordinate system to generate quadrature current (called $I_q$ current) and direct current (called $I_d$ current) values in a rotating reference frame in step 67. Quadrature current is used to control the torque to rotate the impeller and direct current is used to control the attraction force between rotor and stator to control the impeller position. In step 68, the next quadrature voltage is determined by the quadrature current error between the quadrature current transformed from step 67 and the required current for impeller rotation. In step 69, the next direct voltage is determined by the direct current error between the direct current transformed from step 67 and the required current for the attraction force alternation to control the impeller position. In step 70, the quadrature and direct voltage are transformed back to the stationary reference frame in order to provide the multiphase voltage commands which are output to the PWM circuit.

Figure 9:
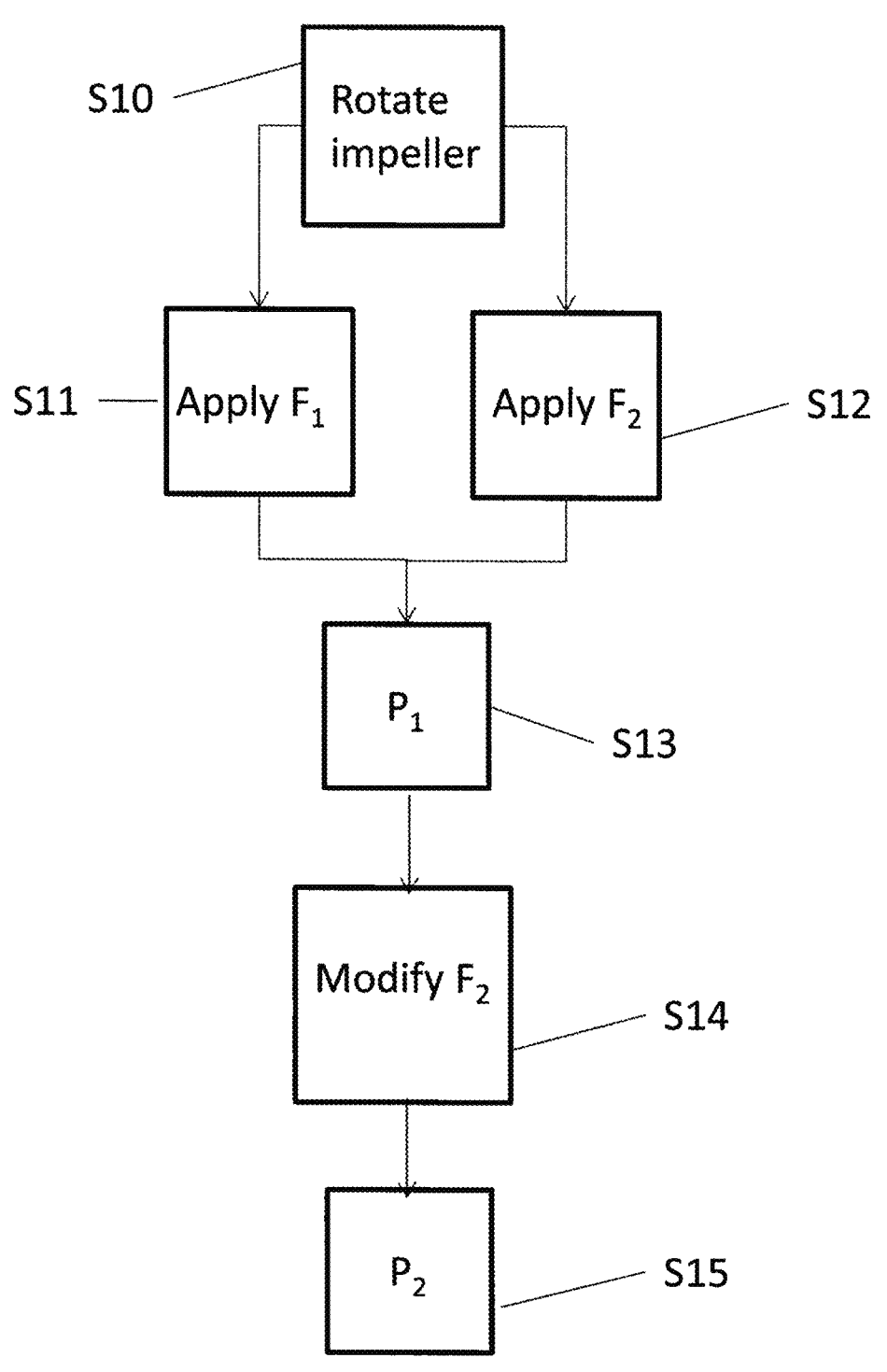
FIG. 9 is a flowchart showing a method of moving the impeller in accordance with the invention.

FIG. 9 is a flowchart showing another method of operating a rotary machine in accordance with the invention. The method includes operating the pump to rotate the impeller by applying a rotating magnetic field in step S10. During operation the impeller is levitated and positioned at a balanced position (P$_1$) by a balancing of forces. As described above, in an exemplary embodiment the impeller is levitated by the combination of hydrodynamic forces $F_1$ and other bearing forces $F_2$ (e.g., stator attractive force, passive magnetic forces, and/or bulk forces like gravity) in steps S11 and S12. Next, at least one of the forces, $F_2$, is modified to place the impeller out of balance in step S14. The impeller moves to a new position, $P_2$, where the forces are once again balanced in step S15.

Figure 10:
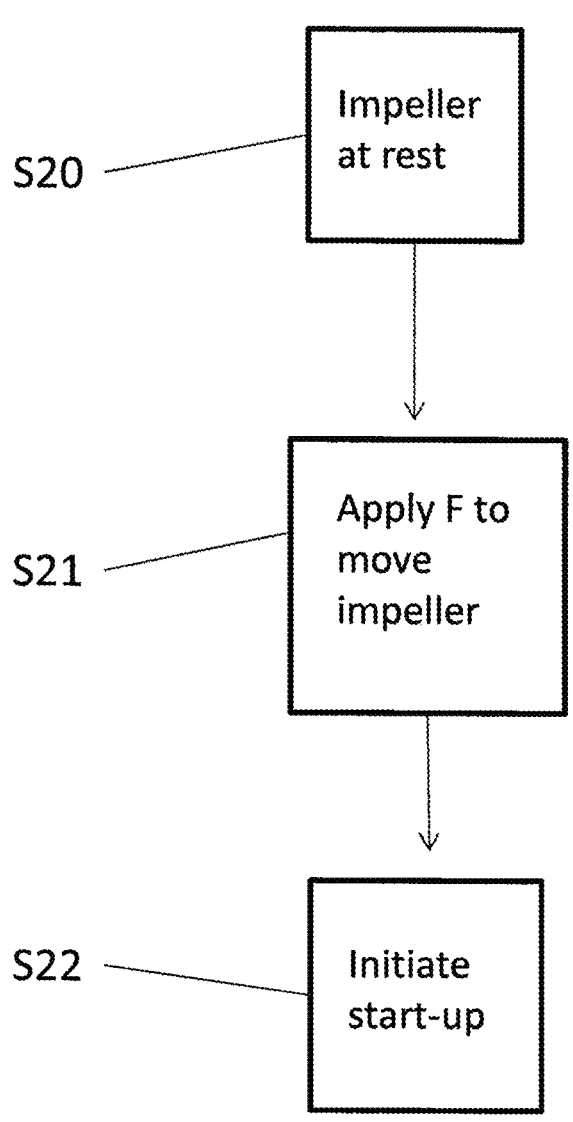
FIG. 10 is a flowchart showing a method of starting up a pump in accordance with the invention.

Turning to FIG. 10, in one embodiment, the impeller position control technique is used to facilitate start-up of the pump. In step S20, the exemplary pump is configured so the impeller rests against the inlet side (top of the housing) when the impeller is not rotating. In a typical pump with hydrodynamic forces alone, or in combination with magnetic forces, the impeller is levitated away from the wall as it rotates. The blood entrained in the gap between the impeller and the housing creates hydrodynamic pressure; however, the impeller must be rotating at a sufficient speed to create the hydrodynamic pressure. Until the minimum speed is met, the impeller rubs against the housing wall. In the exemplary pump, by contrast, the impeller is pulled away from the wall prior to, or just after, rotation begins thereby eliminating the deleterious effects of friction. The impeller is pulled away from the wall by applying a force, F, as described above in step S21. For example, the commutation angle may be modified to exert an attractive force. Referring to FIG. 7, by example, the pump can be configured so the impeller rests at the inlet side. By applying an attractive force to the motor side the impeller moves down from the top wall. In step S22, the regular start-up sequence is initiated after the impeller is removed from the wall.

Figure 11:
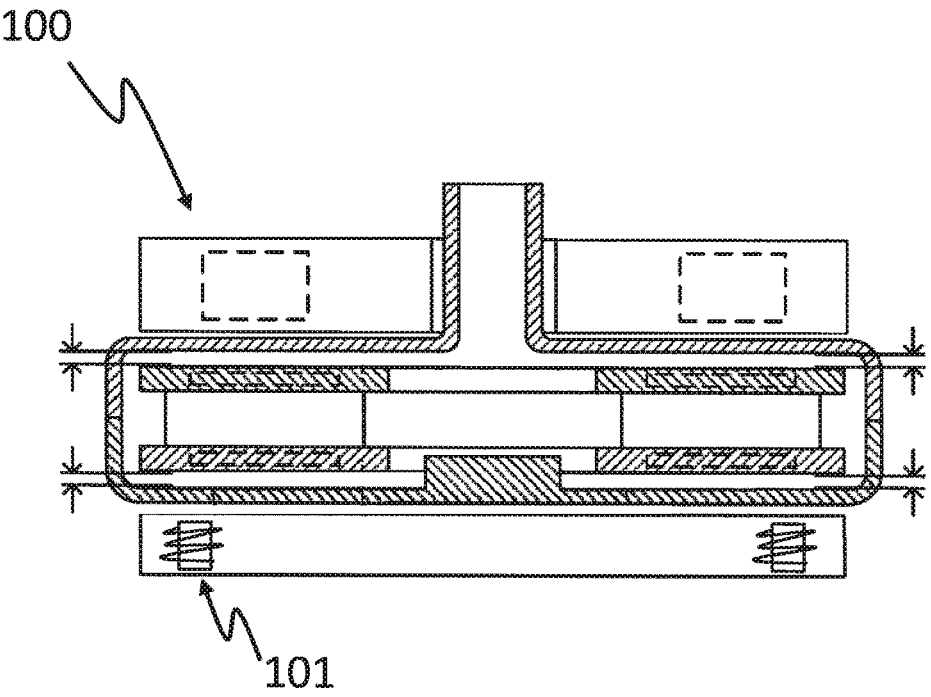
FIG. 11 is a cross-sectional view of a centrifugal flow pump in accordance with aspects of the invention, illustrating a supplemental electromagnetic bearing.

FIG. 11 shows a rotary machine in accordance with another embodiment making use of electromagnets. Pump 100 in FIG. 11 is similar in various respects to pump 10 in FIG. 3. In the exemplary embodiment, however, pump 100 includes an active electromagnetic (EM) system 101. The EM force generated by electromagnets is used primarily or adjunctively to move the impeller. Exemplary electromagnets 101 comprise iron cores and windings. The EM force is modified in a conventional manner by changing the current applied to the windings. The application of the EM force causes the impeller to move to position $P_{E2}$. One will appreciate that the EM force can overpower hydrodynamic and passive magnetic forces present in the system. Accordingly, the EM structure must dimensioned and configured to apply a relatively balanced force. An advantage of using electromagnets over the existing stator assembly is that there is relatively greater positional control over the impeller. By contrast, as described above, the phase currents typically cannot be used as the primary variable to adjust the axial attractive force on the impeller. A disadvantage of this embodiment is the need to provide an entirely separate EM system. This may not be an issue with large industrial rotary machines, but many types of motors have restrictive form factors. For example, implanted pumps must be relatively small in order to address a wider patient population.

Figure 12:
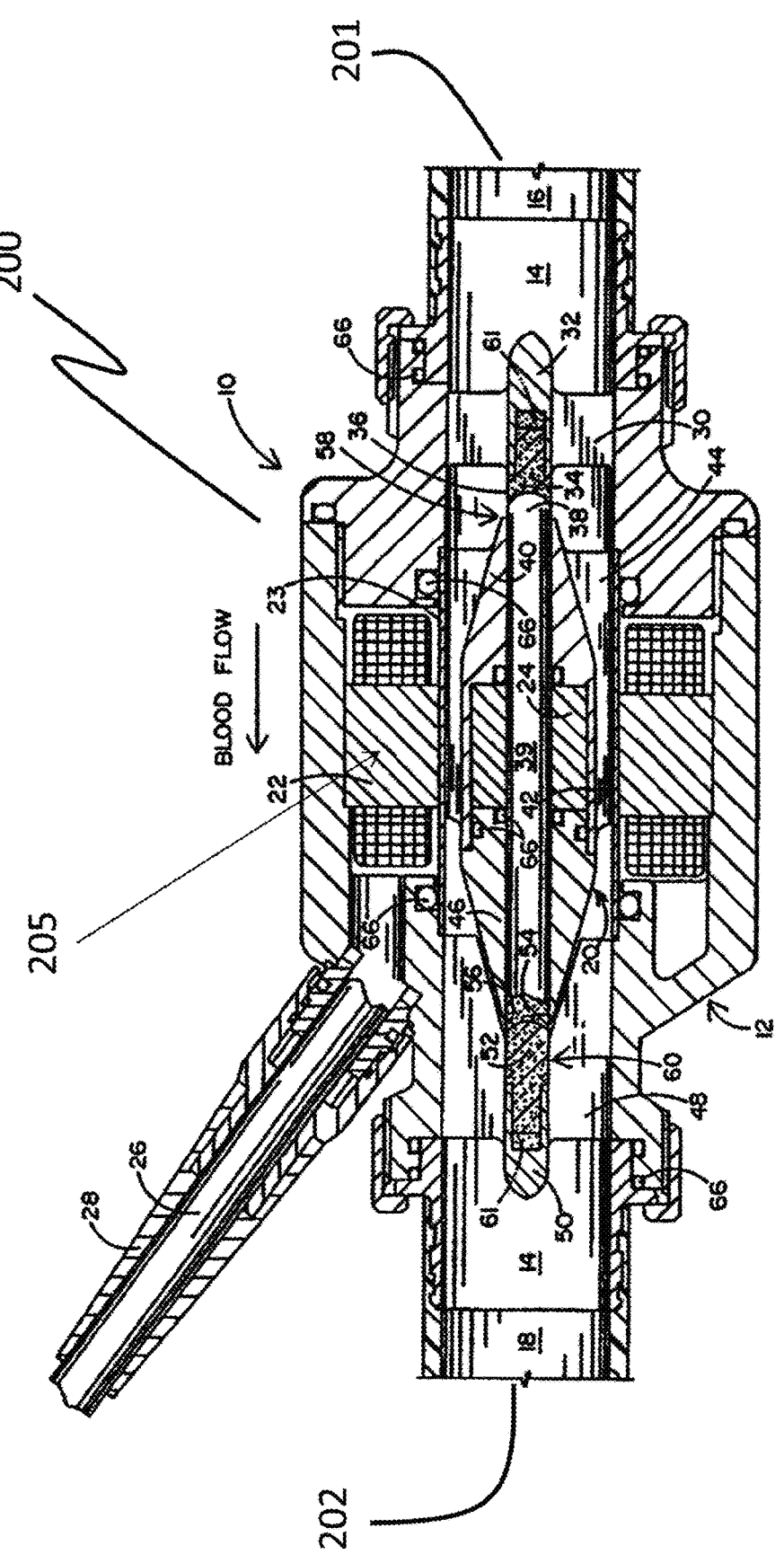
FIG. 12 is a cross-sectional view of an axial flow pump in accordance with aspects of the invention, the axial flow pump including mechanical bearings.
Figure 13:
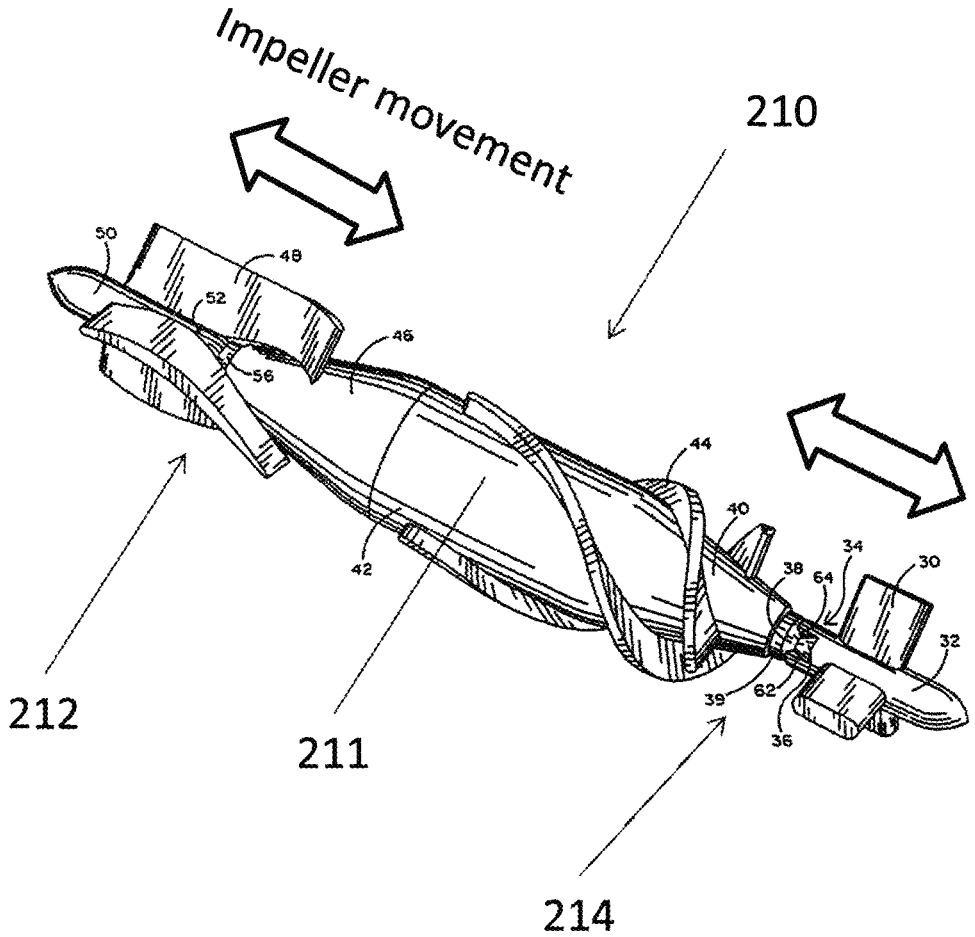
FIG. 13 is a perspective view of the impeller of FIG. 12, with arrows depicting the direction of translation in accordance with the invention.

FIGS. 12 and 13 illustrate another implantable pump in accordance with the invention. Pump 200 is similar in various respects to pumps 10 and 100 described above except pump 200 is an axial flow pump. Blood flows from in through inlet 201 and out through outlet 202 in a generally linear, axial direction. Pump 200 includes an impeller 210 having blades for moving blood through the pump housing and imparting kinetic energy in the fluid.

Impeller 210 is fixed within the housing by ball-and-cup bearings 212 and 214. The ball-and-cup bearings are closely toleranced and generally fix the impeller in a specific position. However, the exemplary bearings are lubricated and washed by the blood flow around the impeller. Accordingly, there is some fluid between the ball and cup surfaces.

Torque is applied to the impeller by a stator assembly 205. The stator assembly 205 includes windings and is driven using a FOC algorithm in a similar manner to the stator assemblies described above. In practice, the impeller position is adjusted proceeding according to the method shown in FIGS. 5 and/or 9. Using the FOC technique described above the impeller is rotated in the pump housing. At a desired time the $I_d$ current is modulated to adjust the attractive force on the impeller in the axial direction. As long as the attractive force is sufficient to squeeze blood out from a respective bearing gap, the impeller will move axially towards inlet 201 or outlet 202. The bearing gaps of pump 200 are relatively small compared to Gap 1 and Gap 2 of pump 50 in FIG. 4. However, even relatively small impeller movement may be beneficial to enable control of the bearing gaps.

The method of adjusting the pump gaps to increase the washout rate may be particularly beneficial in pump designs with mechanical bearings. The relatively small gaps in the bearings mean that there is very little fluid flow and thus a higher risk of thrombus. The greater friction also can contribute to greater thrombus risk. Accordingly, the ability to increase the gap between the ball and the cup, even on a small scale, can lead to significant improvements in outcomes.

Figure 14:
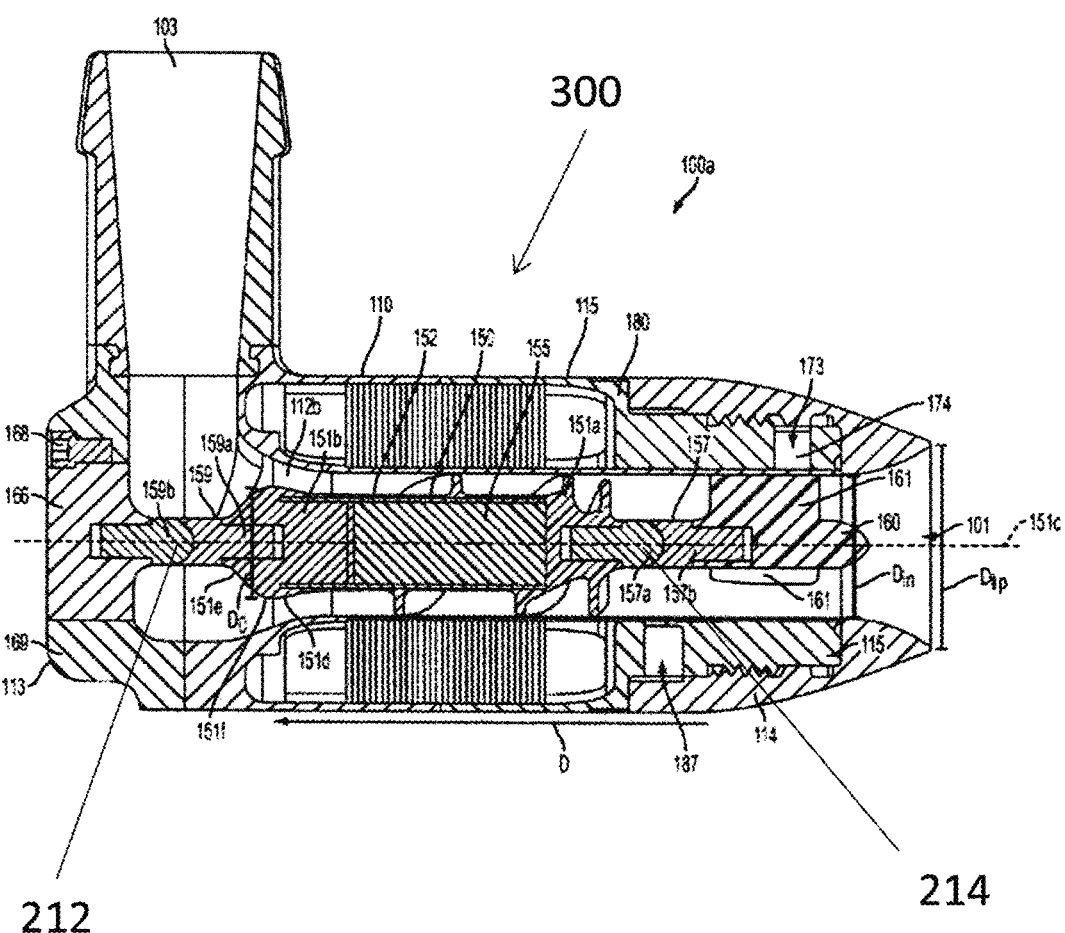
FIG. 14 is a cross-sectional view of an axial flow pump in accordance with aspects of the invention.

FIG. 14 illustrates another pump 300 similar to pump 200. Pump 300 includes an impeller fixed between two mechanical bearings 212 and 214. Pump 300 is slightly different than pump 200 because the outlet extends at an angle from the inlet. Pump 300 is configured in a relatively compact design compared to pump 200 including a relatively smaller stator assembly; however, the same general principles can be applied to control the motor and adjust the impeller position.

Figure 15:
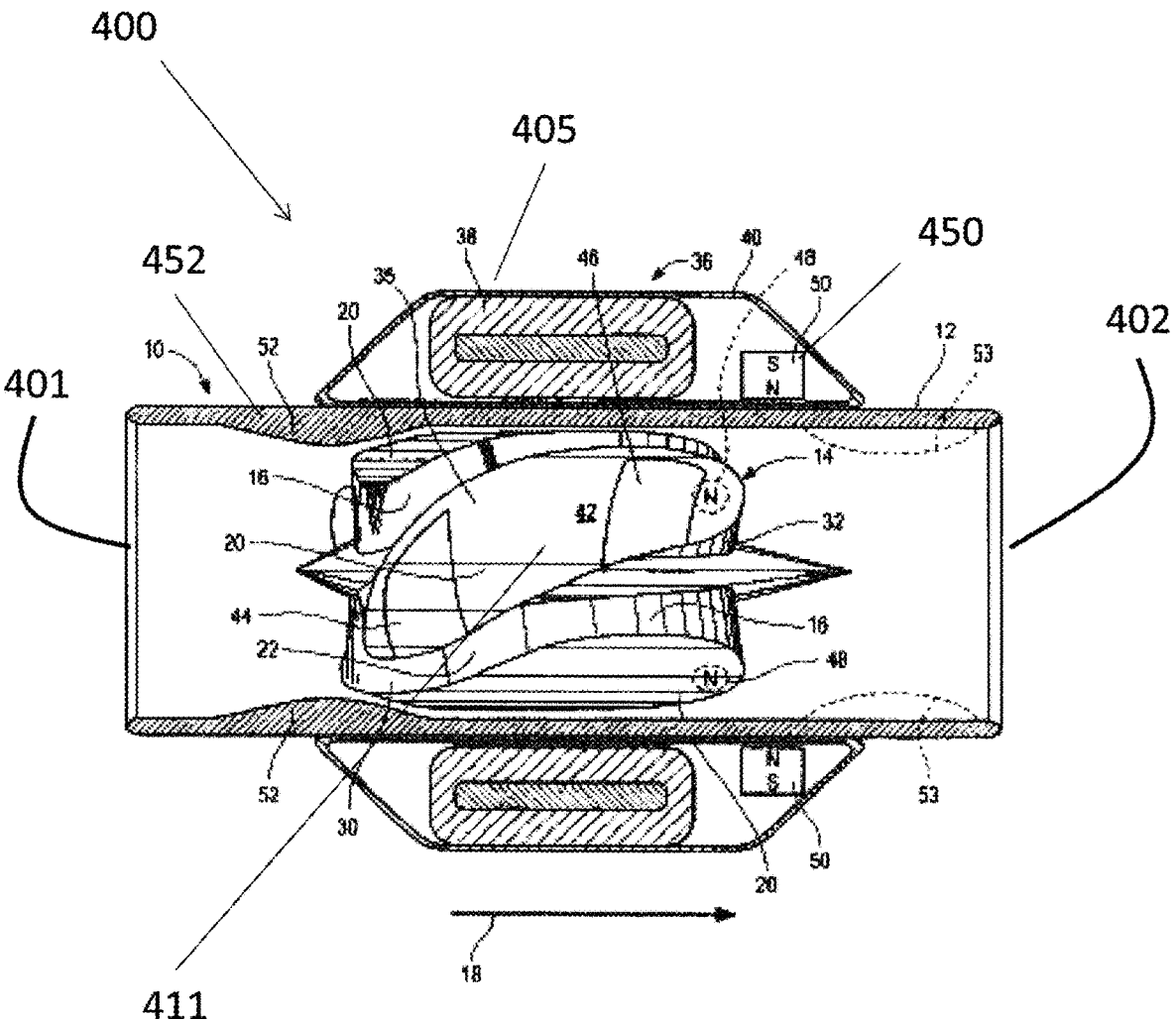
FIG. 15 is a cross-sectional view of an axial flow pump in accordance with aspects of the invention, the axial flow pump including hydrodynamic and magnetic bearings.

FIG. 15 is a cross-sectional view of another pump 400 similar to pumps 200 and 300, except pump 400 is an axial flow pump with non-contact bearings. Pump 400 includes a pump housing having an inlet 401 and outlet 402. An impeller 411 is positioned within a pump chamber for imparting flow to the blood fluid within the housing. The impeller is entirely formed of a magnetic material which is driven by interaction with a stator assembly 405.

Impeller 411 is stabilized in the pump chamber by a combination of hydrodynamic and passive magnetic forces. Impeller 411, which is a magnetic material, interacts with the magnetic material in stator assembly 405 to provide an axial centering force. A pump ring 452 with a chamfer surface is positioned at the leading end of the impeller to create hydrodynamic stabilization forces in the axial direction (left to right) and radial direction (up and down on page). A permanent magnet ring 450 is provided at the trailing edge of the impeller is oriented with a north pole facing a north pole of the impeller. This arrangement creates an axial bias force to push the impeller against the pump ring 452. The magnet ring 450 also provides a radially centering force. Finally, the impeller includes deep hydrodynamic grooves to generate a hydrodynamic pressure force against the inner walls of the pump chamber for radial stabilization.

In operation, the impeller remains stable in the axial and radial directions. There may be some axial movement as the rotational speed of the impeller changes or as a result of other forces (e.g., the native pulse), but generally the impeller remains centered below the stator assembly.

Using the FOC control technique described above, the attractive force of the stator assembly 405 on impeller 411 can be modified. In one embodiment, pump 400 is configured so impeller is eccentric when centered below the stator assembly 405. In this example, increasing the attractive force amounts to an increase in the axial stiffness to resist axial movement. In one embodiment, the attractive force is modified to actually move impeller 411 axially. For example, the impeller can be moved closer to pump ring 452 to squeeze blood out of the gap between impeller 411 and a surface of ring 452. The impeller may also be moved away from ring 452 to increase the blood gap therebetween. In this manner, the impeller position control technique adds an element of active position control otherwise not possible with the passive bearing configuration of pump 400.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A mechanical circulatory support system comprising:
a ventricular assist device comprising a housing, an impeller, levitation magnets, a stator assembly, and control electronics, wherein the housing defines an inlet, a pump chamber, and an outlet, wherein the impeller is disposed and configured for magnetic suspension within the pump chamber, wherein the impeller comprises a first annular disk, a second annular disk, centrifugal impeller blades, first magnet segments, and second magnet segments, wherein the centrifugal impeller blades are disposed between the first annular disk and the second annular disk, wherein the first magnet segments are embedded in the first annular disk, wherein the second magnet segments are embedded in the second annular disk, wherein the stator assembly is disposed adjacent to the pump chamber so that the first annular disk is disposed between the stator assembly and the centrifugal impeller blades, wherein the stator assembly comprises stator coils operable to generate a stator magnetic field that interacts with the first magnet segments to rotate the impeller within the pump chamber and apply a first positioning force to the impeller, wherein the levitation magnets are disposed adjacent to the pump chamber so that the second annular disk is disposed between the levitation magnets and the centrifugal impeller blades so that the levitation magnets apply a second positioning force to the impeller, and wherein the control electronics are disposed within the housing and configured to control currents supplied to the stator coils to generate the stator magnetic field to control rotation of the impeller within the pump chamber and to control a magnitude of the first positioning force applied to the impeller to control an axial position of the impeller in the pump chamber;
a percutaneous cable connected to the ventricular assist device;
an external control unit connected to the ventricular assist device via the percutaneous cable; and
an external power source connected to the external control unit.

2. The mechanical circulatory support system of claim 1, wherein:
the ventricular assist device comprises impeller positions sensors configured to generate impeller position sensor output indicative of axial positions of the impeller in the pump chamber; and
the control electronics are configured to control phase voltages applied to the stator coils further based on the impeller position sensor output to control the axial position of the impeller in the pump chamber.

3. The mechanical circulatory support system of claim 2, wherein impeller position sensors are disposed adjacent to the pump chamber so that the first magnet segments are disposed between the impeller position sensors and the centrifugal impeller blades.

4. The mechanical circulatory support system of claim 1, wherein the second annular disk is parallel to the first annular disk.

5. The mechanical circulatory support system of claim 1, wherein:
the impeller has an impeller axis of rotation; and

the inlet is axially aligned with the impeller axis of rotation when the impeller is centered within the pump chamber.

6. The mechanical circulatory support system of claim 1, wherein:
the first annular disk defines a first annular disk central aperture; and
the housing comprises a protruding hub that extends into the first annular disk central aperture.

7. The mechanical circulatory support system of claim 1, wherein the external control unit comprises an internal battery.

8. The mechanical circulatory support system of claim 1, wherein the external power source comprises an external battery.

9. The mechanical circulatory support system of claim 1, wherein:
the housing defines a volute region through which blood flow output from the impeller is conveyed to the outlet;
a first member of the housing defines the inlet and partially defines each of the pump chamber, the volute region, and the outlet; and
a second member of the housing partially defines each of the pump chamber, the volute region, and the outlet.

10. The mechanical circulatory support system of claim 9, wherein the housing includes a flow-dividing guide wall disposed within the volute region.

11. The mechanical circulatory support system of claim 1, wherein the stator assembly is a three-phase stator assembly.

12. The mechanical circulatory support system of claim 1, wherein the stator assembly is disposed between the control electronics and the pump chamber.

13. The mechanical circulatory support system of claim 1, wherein:
the levitation magnets produce a stationary magnetic field that attracts the second magnet segments towards the levitation magnets; and
the stator assembly is configured for generating a rotating magnetic field that attracts the first magnetic segments towards the stator assembly.

14. A mechanical circulatory support system comprising:
a ventricular assist device comprising a housing, an impeller, levitation magnets, a stator assembly, and control electronics, wherein the housing defines an inlet, a pump chamber, and an outlet, wherein the impeller is disposed and configured for magnetic suspension within the pump chamber, wherein the impeller comprises a first annular disk, a second annular disk, centrifugal impeller blades, first magnet segments, and second magnet segments, wherein the centrifugal impeller blades are disposed between the first annular disk and the second annular disk, wherein the first magnet segments are embedded in the first annular disk, wherein the second magnet segments are embedded in the second annular disk, wherein the stator assembly is disposed adjacent to the pump chamber so that the first annular disk is disposed between the stator assembly and the centrifugal impeller blades, wherein the stator assembly comprises stator coils operable to generate a stator magnetic field that interacts with the first magnet segments to rotate the impeller within the pump chamber and apply a first positioning force to the impeller, wherein the levitation magnets are disposed adjacent to the pump chamber so that the second annular disk is disposed between the levitation magnets and the centrifugal impeller blades so that the levitation magnets apply a second positioning force to the impeller, and wherein the control electronics comprise motor drive power electronics operable to control phase voltages applied to the stator coils to generate the stator magnetic field to control rotation of the impeller within the pump chamber and to control a magnitude of the first positioning force applied to the impeller;

a percutaneous cable connected to the ventricular assist device;

an external control unit connected to the ventricular assist device via the percutaneous cable; and an external power source connected to the external control unit.

15. The mechanical circulatory support system of claim 14, wherein the control electronics employ a motor control algorithm to control the phase voltages applied to the stator coils.

16. The mechanical circulatory support system of claim 14, wherein the control electronics are configured to:

determine a target quadrature current based on a target rotational rate for the impeller;

determine a target direct current based on a target axial position for the impeller; and control the motor drive power electronics based on the target quadrature current and the target direct current.

17. The mechanical circulatory support system of claim 16, wherein:

the ventricular assist device comprises impeller positions sensors configured to generate impeller position sensor output indicative of axial positions of the impeller in the pump chamber; and the control electronics are configured to determine the target direct current further based on the impeller position sensor output.

18. The mechanical circulatory support system of claim 17, wherein the control electronics comprise a current sensing circuit configured to determine measured phase currents in the stator coils, and wherein the control electronics are further configured to:

estimate current rotational speed and current angle of the impeller based on the measured phase currents;

transform the measured phase currents into a two-axis rotating coordinate system to determine a measured quadrature phase current and a measured direct phase current;

determine the target quadrature current based on the measured quadrature phase current and the target rotational rate for the impeller;

determine an axial position deviation of the impeller based on the impeller position sensor output;

determine the target direct current based on the measured direct phase current and the axial position deviation of the impeller;

transform the target quadrature current and the target direct current back to determine target phase currents for the stator coils in a reference stationary reference frame; and control the motor drive power electronics based on the target phase currents to apply phase voltages to the stator coils.

19. The mechanical circulatory support system of claim 16, wherein the target rotational rate for the impeller is based on one or more monitored patient physiological parameters.

20. The mechanical circulatory support system of claim 14, wherein the control electronics are configured to control the motor drive power electronics to implement a start-up sequence in which the stator coils are controlled to magnetically levitate the impeller prior to rotating the impeller.

* * * * *